(12) United States Patent
Samonte et al.

(10) Patent No.: US 11,822,878 B2
(45) Date of Patent: Nov. 21, 2023

(54) SYSTEMS, METHODS AND DEVICES FOR STRUCTURED DYNAMIC ELECTRONIC FORMS

(71) Applicant: Think Research Corporation, Toronto (CA)

(72) Inventors: Emimel Samonte, Toronto (CA); Kirsten Lewis, Toronto (CA); Daniel Karas, Toronto (CA); Ben Hare, Toronto (CA)

(73) Assignee: Think Research Corporation, Toronto (CA)

( * ) Notice: Subject to any disclaimer, the term of this patent is extended or adjusted under 35 U.S.C. 154(b) by 0 days.

(21) Appl. No.: 17/679,365

(22) Filed: Feb. 24, 2022

(65) Prior Publication Data

US 2022/0269852 A1 Aug. 25, 2022

Related U.S. Application Data

(60) Provisional application No. 63/153,135, filed on Feb. 24, 2021.

(51) Int. Cl.
*G06F 17/10* (2006.01)
*G06F 40/174* (2020.01)
(Continued)

(52) U.S. Cl.
CPC .......... *G06F 40/174* (2020.01); *G06F 40/186* (2020.01); *G06F 40/197* (2020.01)

(58) Field of Classification Search
CPC ..... G06F 40/174; G06F 40/186; G06F 40/197
See application file for complete search history.

(56) References Cited

U.S. PATENT DOCUMENTS

| 6,466,937 B1 * | 10/2002 | Fascenda | G06F 16/957 |
| | | | 707/999.102 |
| 6,560,604 B1 * | 5/2003 | Fascenda | H04L 9/40 |
| | | | 707/999.1 |

(Continued)

FOREIGN PATENT DOCUMENTS

| CA | 2889996 C | * 12/2020 | ............. G06F 16/00 |
| CN | 101313299 A | * 11/2008 | ........... G06F 17/243 |

(Continued)

OTHER PUBLICATIONS

European Patent Office, Extended European Search Report for EP Patent App. No. 22020079.4, dated Jun. 27, 2022.

*Primary Examiner* — Shahid K Khan
(74) *Attorney, Agent, or Firm* — Own Innovation; James W. Hinton

(57) ABSTRACT

Computer systems, methods, and devices for structured dynamic electronic forms are provided. The system includes a user device comprising a client form management application and a server comprising a server form management application. The client form management application generates and sends a request for a dynamic electronic form to the server. The server form management application stores the dynamic electronic form comprising separately stored form template data and form data; and merges and sends the form template data and the form data to the user device for rendering. The client form management application sends a request for a form filler package ("FFP") comprising rules for filling out and rendering the dynamic electronic form. The server form management application sends the FFP to the user device and the client form management application renders the dynamic electronic form using the merged form template data and form data and the FFP.

20 Claims, 11 Drawing Sheets

(51) Int. Cl.
*G06F 40/186* (2020.01)
*G06F 40/197* (2020.01)

(56) References Cited

U.S. PATENT DOCUMENTS

| | | | | |
|---|---|---|---|---|
| 6,615,199 | B1* | 9/2003 | Bowman-Amuah | G06F 9/449 706/50 |
| 6,820,235 | B1* | 11/2004 | Bleicher | G16H 70/40 715/236 |
| 7,698,628 | B2* | 4/2010 | Perelman | G06F 40/174 715/756 |
| 7,734,995 | B1* | 6/2010 | Saikaly | G06F 40/186 715/209 |
| 7,779,345 | B2* | 8/2010 | Topalov | G06F 15/167 715/224 |
| 9,430,114 | B1* | 8/2016 | Dingman | G06F 16/25 |
| 11,138,287 | B1* | 10/2021 | Botero | G06F 40/146 |
| 2002/0129033 | A1* | 9/2002 | Hoxie | G16H 70/60 |
| 2002/0178190 | A1* | 11/2002 | Pope | G06F 16/972 707/E17.117 |
| 2002/0194219 | A1* | 12/2002 | Bradley | G06F 40/117 725/9 |
| 2004/0083426 | A1* | 4/2004 | Sahu | G06F 40/174 715/224 |
| 2005/0125321 | A1* | 6/2005 | Gerstner | G06Q 20/385 705/42 |
| 2006/0004651 | A1* | 1/2006 | Corr | G06Q 40/02 705/38 |
| 2006/0020886 | A1* | 1/2006 | Agrawal | G06F 40/174 715/256 |
| 2006/0136810 | A1* | 6/2006 | Truong | G06F 40/174 715/222 |
| 2006/0150086 | A1* | 7/2006 | Griffin | G06F 40/143 715/235 |
| 2007/0300145 | A1* | 12/2007 | Perelman | G06F 40/174 707/999.001 |
| 2008/0028289 | A1* | 1/2008 | Hicks | G06F 40/174 715/224 |
| 2008/0154937 | A1* | 6/2008 | Sattler | G06F 9/451 707/999.102 |
| 2008/0172598 | A1* | 7/2008 | Jacobsen | G06Q 30/0613 715/224 |
| 2008/0307298 | A1* | 12/2008 | Matveief | G06F 40/174 715/224 |
| 2009/0183063 | A1* | 7/2009 | Malkin | G06Q 10/06 718/100 |
| 2011/0320605 | A1* | 12/2011 | Kramer | H04L 67/1097 709/226 |
| 2013/0167111 | A1* | 6/2013 | Moore | G06F 8/38 717/105 |
| 2014/0033011 | A1* | 1/2014 | Wandeler | G06F 40/174 707/E17.118 |
| 2014/0108043 | A1 | 4/2014 | Ach et al. | |
| 2015/0169534 | A1* | 6/2015 | Meschkat | G06F 40/143 715/234 |
| 2015/0358424 | A1* | 12/2015 | Braun | H04L 67/56 709/219 |
| 2016/0062973 | A1* | 3/2016 | Haines | G06F 40/174 715/224 |
| 2017/0192948 | A1* | 7/2017 | Gaither | G06F 40/174 |
| 2017/0300634 | A1* | 10/2017 | Chiang | G16H 10/60 |
| 2020/0097268 | A1* | 3/2020 | Olsson | G06F 8/38 |
| 2020/0110793 | A1* | 4/2020 | Sullivan | G06F 40/14 |
| 2020/0152297 | A1* | 5/2020 | Freeburg, II | G16H 20/60 |

FOREIGN PATENT DOCUMENTS

| | | | | |
|---|---|---|---|---|
| EP | 1777629 | A1 * | 4/2007 | G06F 16/958 |
| KR | 20140126311 | A * | 10/2014 | |
| WO | WO-2006010737 | A2 * | 2/2006 | G06F 17/243 |

* cited by examiner

SYSTEMS, METHODS AND DEVICES FOR STRUCTURED DYNAMIC ELECTRONIC FORMS

TECHNICAL FIELD

The following relates generally to electronic data entry forms, and more particularly to systems and methods for storing, processing, and visualizing healthcare-related electronic data entry forms.

INTRODUCTION

Forms are commonly used for gathering information and can be particularly important in the healthcare context for the acquisition of medical and clinical data. Forms simplify the process of providing information, such as by presenting users with instructions on what information should be provided in the appropriate spaces and may also present users with a multitude of options from which they can conveniently select in order to provide or add data to the form (e.g. checkboxes).

In recent years, the use of electronic forms has become increasingly popular, at least in part due to capabilities not possible with paper-based data. While the healthcare community has joined this transition towards electronic documentation, such as through the computerization of patient records and the like, there is still some reluctance or hesitation to adopt electronic data entry forms in some applications due to the nature of the data being recorded and stored and limitations on the types of electronic forms available.

In particular, web-based data approaches to electronic data entry forms are becoming increasingly popular, at least in part due to the accessibility and viewability of web-based data via Internet Browsers and web-enabled applications. Web-based data formats are readily digitally communicable and processable across a variety of devices. Non-limiting examples of relatively common web-based data include HTML data, XML data, JSON data, JavaScript data, and the like.

Electronic data entry forms may include single-use and multiple-use forms. Single-use forms may be used once to input data, whereas multiple-use forms may be used multiple times to provide input data to the form. For example, a multiple-use form may be revisited by a user multiple times to provide or add data to the form. This may include adding new data to a data entry field that has previously received data or adding data to a previously unused data entry field. In some cases, the data provided to the multiple-use form in each instance of use may have relevance and should be maintained by the form for a complete record. An example of a single-use healthcare form may be an order set. An example of a multiple-use healthcare form is a form, such as a "clinical note" or the like, that is used to track a patient's condition across multiple related encounters (e.g. progress note). Use of such a form may occur during a hospital stay where a physician creates a clinical note as they see each patient (e.g. on their daily rounds). Further, a multiple-use form may also need to add a new section to an existing form-instance, or add different sections (possibly in different orders), for a particular form-type that is created for multiple patients.

In some cases, it may be desired to have an electronic form type that can maintain a history of inputted data associated with one or more form fields. A clinical note form is one example. If data entered into a form field is changed over time, it may be desirable to store and retain information of the change (e.g. what was changed and when) as that is data that is useful to the viewer of the form. In contrast, many traditional electronic forms may have data entry fields that can be checked and then unchecked and such change information is not valuable to the viewer of the form (e.g. single-use form, order set).

Electronic data entry forms that need to have a history associated with one or more data entry fields may have to be saved and stored in a completely different way compared to electronic forms without a need to store such history of data entry.

One option to solve this problem is to embed rules on how to read and fill out a data entry form in the form-using application. Such an approach may become unsustainable, however, as new form types are developed, requiring constant provision of updated packages (e.g. JS packages) to users of the form-using application. Further, such an approach may embed the rules for filling out all form types in the JS package, which may be subject to reverse engineering.

Accordingly, systems and methods are desired that overcome one or more disadvantages associated with existing electronic data entry form systems and particularly healthcare-related data entry forms.

SUMMARY

A computer system for storing and visualizing structured dynamic electronic forms is provided. The system includes a user device comprising a client form management application configured to generate, in response to a user input, a first request for a dynamic electronic form, and send the first request to a computer server. The system includes the computer server comprising a server form management application configured to: store the dynamic electronic form in memory, the dynamic electronic form comprising form template data and form data, the form data corresponding to input data inputted to the dynamic electronic form, wherein the form template data and the form data are stored separately, the form template data is stored in a first format, and the form data is stored in a second format; in response to the first request from the user device, merge the form template data and the form data and send the merged form template data and form data to the user device for rendering. The client form management application is further configured to generate, based on form type data associated with the form template data and specifying a form type, a second request for a form filler package for the form type, the form filler package comprising rules for filling out and rendering the dynamic electronic form, and send the second request to the computer server. The server form management application is further configured to, in response to the second request, send the form filling package to the user device. The client form management application is further configured to render, via a form rendering engine, the dynamic electronic form in a user interface using the merged form template data and form data and the form filler package, wherein the rendered dynamic electronic form includes a data entry field for receiving the form data.

The first format may be an unstructured format and the second format may be a structured format.

The form data stored at the computer server may include a history of values for the data entry field, the history of values comprising a plurality of values wherein each of the plurality of values correspond to input data entered into the data entry field during a different instance of use of the dynamic electronic form.

The dynamic electronic form may be configured to store a plurality of values for a given data entry field in the dynamic electronic form as a history of data values. Each of the plurality of data values may correspond to input data received by the given data entry field during a different instance of use of the dynamic electronic form. In some cases, the given data entry field may be configured as a conditional visibility data entry field for controlling visibility of one or more other data entry fields in the dynamic electronic form. In some cases, the given data entry field may be configured as a conditional ordering data entry field for controlling relative positioning or ordering (e.g. vertical ordering) of a first data entry field relative to a second data entry field. In some cases, conditional ordering may be implemented such that the order in which data entry fields or other form components in a multi-selection list (e.g. dropdown) are selected is stored and used to order the positioning of the data entry fields or other form components in the dynamic electronic form. In an example, conditional ordering functionality may be implemented in a conditional visibility data entry field such that if a data entry field meets the condition necessary for its display on the dynamic electronic form, the data entry field may then be displayed on the form subject to conditional ordering.

The dynamic electronic form may include a conditional visibility controlling data field which controls whether the data entry field is visible on the dynamic electronic form or not based on a value entered into the conditional visibility controlling data field.

The client form management application may be further configured to send new form data inputted into the data entry field to the computer server for storage with the form data.

The server form management application may be further configured to store the new form data as a historical data value of the data entry field.

The first request may include a first identifier linked to the form data and usable by the server form management application to retrieve the form data and a second identifier linked to the form template data and usable by the server form management application to retrieve the form template data.

Retrieving the form template data may include retrieving a latest template version of the form template data.

The server form management application may be further configured to convert the merged form template data and form data into a lightweight data exchange format prior to send to the user device.

The server form management application may use the first identifier to determine whether the dynamic electronic form has existing form data and either retrieve the existing form data or create a new dynamic electronic form based on the determination.

A computer device for structured dynamic electronic forms is also provided. The device includes a processor and a memory in communication with the processor. The processor is configured to execute a form management application to: store a dynamic electronic form including in memory, the dynamic electronic form comprising form template data and form data, the form data corresponding to input data inputted to the dynamic electronic form, wherein the form template data and the form data are stored separately, the form template data is stored in a first format, and the form data is stored in a second format; in response to a first request received from a user device, merge the form template data and the form data and send the merged form template data and form data to the user device for rendering; and in response to a second request from the user device requesting a form filling package corresponding to a form type of the dynamic electronic form, retrieve and send the form filling package to the user device, the form filling package comprising rules usable by a form rendering engine of the user device for filling out and rendering the dynamic electronic form, the dynamic electronic form including a data entry field for receiving the form data.

The first format may be an unstructured format and the second format may be a structured format.

The form data may include a history of values for the data entry field, the history of values comprising a plurality of values each of which correspond to input data entered into the data entry field during a different instance of use of the dynamic electronic form.

The server form management application may be further configured to receive new form data from the user device and store the new form data as a historical data value of the data entry field.

The first request may include a first identifier linked to the form data and usable by the form management application to retrieve the form data and a second identifier linked to the form template data and usable by the form management application to retrieve the form template data.

The server form management application may use the first identifier to determine whether the dynamic electronic form has existing form data and either retrieve the existing form data or create a new dynamic electronic form based on the determination.

A computer-implemented method of storing and visualizing structured dynamic electronic forms is also provided. The method includes: storing a dynamic electronic form at a computer server, the dynamic electronic form comprising form template data and form data, the form data corresponding to input data inputted to the dynamic electronic form, wherein the form template data and the form data are stored separately, the form template data is stored in a first format, and the form data is stored in a second format; generating at a user device, in response to a user input, a first request requesting the dynamic electronic form, and sending the first request to the computer server; in response to the first request from the user device, merging the form template data and the form data at the computer server and sending the merged form template data and form data from the computer server to the user device for rendering; generating at the user device, based on form type data associated with the form template data and specifying a form type, a second request requesting a form filler package for the form type, the form filler package comprising rules on how to fill out and render the dynamic electronic form; sending the second request from the user device to the computer server; in response to the second request, sending the form filling package from the computer server to the user device; and rendering, at the user device, the dynamic electronic form in a user interface using the merged form template data and form data and the form filler package, the dynamic electronic form including a data entry field for receiving the form data.

The first format may be an unstructured format and the second format may be a structured format.

Storing the form data at the computer server may include maintaining a history of values for the data entry field, the history of values comprising a plurality of values wherein each of the plurality of values correspond to input data entered into the data entry field during a different instance of use of the dynamic electronic form.

The method may include sending new form data inputted into the data entry field from the user device to the computer server for storage with the form data; and storing the new form data at the computer server as a historical data value of the data entry field.

Other aspects and features will become apparent, to those ordinarily skilled in the art, upon review of the following description of some exemplary embodiments.

BRIEF DESCRIPTION OF THE DRAWINGS

The drawings included herewith are for illustrating various examples of articles, methods, and apparatuses of the present specification. In the drawings.

DETAILED DESCRIPTION

Figure 1:
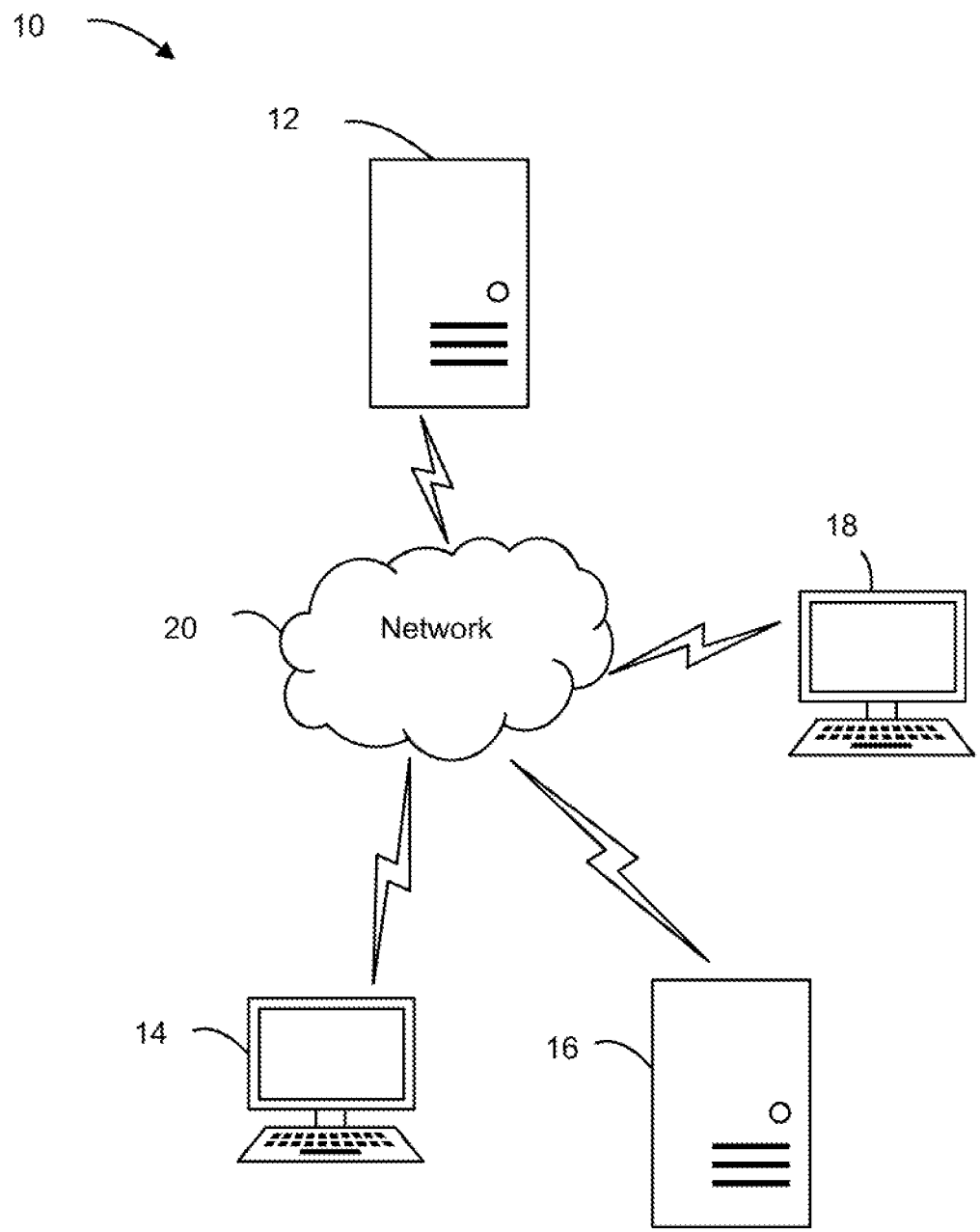
FIG. 1 is a schematic diagram of a system for generating structured clinical notes, according to an embodiment.

Various apparatuses or processes will be described below to provide an example of each claimed embodiment. No embodiment described below limits any claimed embodiment and any claimed embodiment may cover processes or apparatuses that differ from those described below. The claimed embodiments are not limited to apparatuses or processes having all of the features of any one apparatus or process described below or to features common to multiple or all of the apparatuses described below.

One or more systems described herein may be implemented in computer programs executing on programmable computers, each comprising at least one processor, a data storage system (including volatile and non-volatile memory and/or storage elements), at least one input device, and at least one output device. For example, and without limitation, the programmable computer may be a programmable logic unit, a mainframe computer, server, and personal computer, cloud based program or system, laptop, personal data assistance, cellular telephone, smartphone, or tablet device.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device readable by a general or special purpose programmable computer for configuring and operating the computer when the storage media or device is read by the computer to perform the procedures described herein.

A description of an embodiment with several components in communication with each other does not imply that all such components are required. On the contrary, a variety of optional components are described to illustrate the wide variety of possible embodiments of the present invention.

Further, although process steps, method steps, algorithms or the like may be described (in the disclosure and/or in the claims) in a sequential order, such processes, methods and algorithms may be configured to work in alternate orders. In other words, any sequence or order of steps that may be described does not necessarily indicate a requirement that the steps be performed in that order. The steps of processes described herein may be performed in any order that is practical. Further, some steps may be performed simultaneously.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The following relates generally to electronic data entry forms, and more particularly to systems and methods for processing web-based electronic data entry forms which require the maintenance of historically inputted data for one or more data entry fields.

Some electronic data entry forms, such as a web-based fillable progress note form, include one or more data entry fields (e.g. modules) that need to have a history associated with those data entry fields. If data entered into a form field is changed, the electronic form needs to store and retain information on that change (change-related data), such as what was changed and when, as that data is useful to a form viewer. In some cases, the form may be a form that includes certain parts, fields, or even entire sections which comprise a list of modules.

In one aspect, the present disclosure provides a solution where rules on how to read a web-based data entry form do not have to reside in the form-using application itself.

The present disclosure provides systems and methods for a customizable structured dynamic electronic form. This type of form is in contrast to customizable structured static electronic forms, which may also be considered "single-use" forms (in contrast to "multi-use" forms). An example of such a single-use form is an order set form. An order set form is a form that receives input data indicating a group of bundled standard orderables which may represent or include a healthcare provider's instructions or directives to other healthcare workers regarding treatment of a patient. The order set may be a predefined template that provides support in making clinical decisions for a specific condition or medical procedure and provides a grouping of orders that standardizes and expedites the ordering process for a clinical scenario.

For customizable structured static electronic forms, the form is customizable because it can be "built" by selecting and positioning different fields (such as by using a form designing application with a user interface). The form is structured because the different fields (at the time they are selected and placed) can be linked to other fields or to certain concepts or data types in the metadata hierarchy of the form such that the values entered into those fields can be understood and the forms can be analyzed in an automated digital way.

For customizable structured dynamic electronic forms, such as provided by the present disclosure, the forms is customizable because the form can be built by selecting and positioning different form fields or elements (e.g. by using a form designing application such as form designer server 16 or form designer PN2 editor 416, described herein). The form is structured because the different form fields, at the time they are selected and positioned, can be linked to other form fields such that the values entered into the fields can be understood and the forms can be analyzed in an automated digital way. The form is dynamic because, even though the form is built with a set series of fields (e.g. checkboxes, dropdown modules, text fields, etc.), across different usage instances of the form the structure of the form itself changes based on the values entered into the form. In this way, each instance of the form may look completely different from other instances of the form. As a result, there is not simply a "not completed" and "completed" state of the form, but rather the form is a "living document" where each change to the form (i.e. each new field value entered) is saved, as each change can alter the form's structure. This is necessary as historical values entered into certain form fields may need to be retained and stored as part of the form so that, when the user returns to the form (whether the same user or another user), the user can see what values were entered historically (and, in some cases, when such values were entered) and add to those entries rather than overwrite them. In this way, values entered into the form become a part of the form in later versions. The form is also dynamic in that certain modules or parts of the form may need to be hidden, or appear in a different order, based on values entered into earlier fields. In some embodiments, a set of modules or form elements in a form may be linked to a data entry field (e.g. dropdown list) to control whether the set of modules or form elements are displayed on the form and, potentially, in what order the set of modules or form elements appear on the form. For example, if a first module and a second module in a set of modules displayed in a dropdown list data entry field are selected and a third module in the set of modules displayed in the dropdown is not selected, the first and second modules are displayed in the form but the third module is not. In another example, if the second module was selected in the dropdown list data entry field before the first module was selected, the second module may be displayed above the first module on the form.

Accordingly, in some cases, the forms of the present disclosure may operate such that values entered into data entry fields in the dynamic electronic form can alter the visibility of certain other data entry fields or other form components on the form (conditional visibility) or can alter the ordering of data entry fields or other form components on the form (conditional ordering). The data values entered into such conditional visibility or conditional ordering controlling data entry fields (i.e., a data entry field on the form that controls the visibility or ordering of one or more other data entry fields on the form) may be stored similarly to other values entered into other data entry fields on the form. For example, a conditional visibility or ordering controlling data entry field may receive a plurality of values that may be stored as a history of data values. As such, in some cases, different form instances of the same form type may have a different appearance based on values entered into one or more conditional visibility controlling or conditional ordering controlling data entry fields on the form.

An example of a customizable structure dynamic electronic form provided by the present disclosure is an electronic progress note. A progress note is used by clinicians and healthcare providers to record and track the progress of a patient's clinical condition over time.

Referring now to FIG. 1, shown therein is a block diagram of a system 10 for electronic data entry forms, according to an embodiment. The system 10 includes an electronic form management server platform 12 (or form management server 12), which communicates with an end user device 14 via a network 20. The end user device 14 can be used by a user, such as a clinician or healthcare professional, to transmit information to and receive information from the form management server 12. The system 10 also includes an electronic form designer server 16, which is communicatively connected to the form management server 12 via the network 20. The electronic form designer server 16 communicates with a client device 18 via the network 20.

In some embodiments, one or more further servers (not illustrated) may be in communication with server 12 via network 20. Such additional servers, such as a database server, may be adapted to perform specific functions related to the creation, storage, and processing of electronic data entry forms. Allowing such functions to occur on remote servers may thereby allow such automated systems to perform such functions without requiring those functions to run on server 12 directly. Such servers may form a distributed system operable to perform analyses at scale. In some embodiments, additional servers may be in different premises than server 12. For example, additional servers could be running in the cloud.

An electronic data entry form as described herein may be a structured document, such as a structured JSON document (or other web-based document), that represents a data entry form, such as a healthcare-related form. A healthcare-related form as used herein includes forms whose purpose includes collecting patient-related data (e.g. clinical data about a patient). The system 10 is configured to consume the JSON document, thereby allowing a user to view, interact with, manipulate, and provide input data to the electronic data entry form.

While embodiments of the present disclosure may be described with reference to progress note forms, it is to be understood that a progress note is just one example of an electronic data entry form and systems and methods described herein may, in variations, be applied to any type of electronic data entry form and in particular to multi-use electronic forms that include content that can be updated or changed one or more times. The progress note form types include modules. The modules have a history associated with one or more form fields. If a field is changed, the note stores and retains information related to the change (e.g. what was changed and when). Such change data is useful to the viewer of the progress note, as the progress note is used to monitor and document a patient's condition over time. In this sense a progress note form is unique because all changes to the form may be relevant or potentially relevant.

The form management server 12 may be a purpose-built machine designed specifically for storing, rendering, and filling out electronic data entry forms and, in particular, healthcare-related data entry forms. In a particular case, the healthcare-related data entry form can be a structured clinical note, such as a progress note. Managing electronic data entry forms may include generating, storing, retrieving, analyzing, rendering, displaying/visualizing, and/or processing form template data and input data (i.e. form data received or generated in response to user input to the form).

In an embodiment, the form management server 12 can be used, along with the user device 14, to render and "fill out" (i.e. receive input data and store input data) the electronic data entry form.

The form designer server 16 may be a purpose-built machine designed specifically for designing, generating, and editing an electronic data entry form template. In an example, the electronic form template may be an electronic progress note form template. Each data entry form may represent a custom user interface corresponding to a particular data entry task. The user interface may be implemented and presented at the user device 14. In an embodiment, the form designer server 16 can be used, along with the client device 18, to build and generate a structured form template representing a progress note or other electronic data entry form. The structured form template may be a structured JSON document.

In a particular embodiment of the system 10, a web-based document (e.g. JSON document) representing any form-type built using the form designer application can be passed, for example via network 20, to the form management server 12 and the form management server 12 is configured to fill out the web-based document. The rules on how to fill out and render the web-based form may exist in the web-based document form itself. In some embodiments, the web-based or electronic form is a "living" form (or "dynamic form"). The term "living form" is meant to refer to the ability of the form to receive user input data over time, such as through multiple uses of the form potentially by multiple users, and for such data to be entered into the form and stored in such a way that such data inputted into the form is stored and can be accessed and viewed by a user when the form is rendered. This may be in contrast to a single use form or other types of forms in which information contained within the form (i.e. inputted into the form) is not updated or added to over time ("static form"). One such example of a living form is an electronic progress note (or simply, progress note), which is a type of form or note used by medical clinicians to record and monitor a patient's progress over time. While embodiments described herein may refer to "progress notes" as the type of form being generated, stored, and rendered, it is to be understood that a progress note is simply one example of a living form and that, in variations of the systems and methods described herein, the living form may be any type of electronic or web-based form for which data can be inputted into over multiple uses and for which input data received by the form may be updated or added to over time.

In an embodiment, the form management server 12 receives and stores an electronic progress note form template provided by the form designer server 16. The form template may be generated by a form designer application implemented at the form designer server 16 and the client device 18. The form template includes a plurality of data entry fields configured to receive input data from a user, such as a clinician, provided at the end-user device 14. In a particular case, input data provided to the progress note form may represent a dynamic situation, such as the condition of a patient. In such a case, certain types of input data may be recorded by the form multiple times. The form management server 12 can be configured to receive and store input data for the progress note in such a way that historical input data (that is, data previously entered into the form via a data entry field) is maintained. By performing such a function, the form management server 12 and the system 10 may facilitate proper and effective monitoring of a dynamic or developing situation (e.g. a clinical situation) via the electronic progress note by ensuring that historical information that can provide important context to a viewer of the form is saved.

In an embodiment, the system 10, in rendering the form, merges the form template with form data (i.e. data previously inputted into the form) to generate the rendered form. This technique may be used as a result of the system 10 being configured to store the form template separately from the form data (whether the form template and form data are stored in separate databases or in separately in the same database). Storing the form template and the form data separately advantageously makes it easier to store a history of a value inputted into the form (i.e. historical values). This may include storing a history for each value in the form. Historical values of a form value may be stored and displayed as a list of values. The storage by the form of historical values is particularly relevant in cases where the form field configured to receive the value may receive different values over time as different information is inputted over different uses. In some cases, the form template may be stored in the system 10 in a database as a template JSON using an unstructured format such as a JSON B format. In contrast, the form data (i.e. the data inputted into and received by the form) is stored in a structured format. For example, the form data may be stored in an organized table format. The data structure storing the form data may also store modifying user data associating a modifying user with any newly received input data (so it is known by the system who input what information to the form and when). Storing such form data in a JSON B or similar format to allow for storage with the form template can be extremely messy. For example, if the template data and form data were stored together, it may be extremely difficult to update the structure of the form (i.e. the form template) without losing the form data. Structural changes to the form via modifying or updating the form template, which can be made easier by the separate storage of form template data and form data by the system 10, may be necessary or desired over time as users decide to change the certain aspects of the form which require modifications at the template level.

The end user computing devices 14 and client device 18 may be network-connected computing devices used to access applications and services through a suitable web browser, terminal emulator, or similar interface from network connected servers such as servers 12 and 16.

The network 20 may be the Internet. The network 20 may be a private local-area network or a wide-area network. The network 20 may be a TCP/IP, X.25, ATM or similar network. The network 20 may be wired or wireless or a combination of both wired and wireless. The network 20 may be a virtual private network such as PPTP. Traffic on the network 20 may be secured using encryption such as by SSL or IPsec. Where data transmitted/received using network 20 relates to health care, securing network traffic may assist compliance with healthcare information privacy laws, e.g. in the U.S., the Health Insurance Portability and Accountability Act (HIPAA) or in Canada, laws such as the Ontario Personal Health Information Protection Act (PHIPA).

The server platforms 12, 16 and devices 14, 18 may be a server computer, desktop computer, notebook computer, tablet, PDA, smartphone, or another computing device. The devices 12, 14, 16, 18 may include a connection with the network 20 such as a wired or wireless connection to the Internet. In some cases, the network 20 may include other types of computer or telecommunication networks. The devices 12, 14, 16, 18 may include one or more of a memory, a secondary storage device, a processor, an input device, a display device, and an output device. Memory may include random access memory (RAM) or similar types of memory. Also, memory may store one or more applications for execution by processor. Applications may correspond with software modules comprising computer executable instructions to perform processing for the functions described below. Secondary storage device may include a hard disk drive, floppy disk drive, CD drive, DVD drive, Blu-ray drive, or other types of non-volatile data storage. Processor may execute applications, computer readable instructions or programs. The applications, computer readable instructions or programs may be stored in memory or in secondary storage or may be received from the Internet or other network 20.

Input device may include any device for entering information into devices 12, 14, 16, 18. For example, input device may be a keyboard, keypad, cursor-control device, touchscreen, camera, or microphone. Display device may include any type of device for presenting visual information. For example, display device may be a computer monitor, a flat-screen display, a projector or a display panel. Output device may include any type of device for presenting a hard copy of information, such as a printer for example. Output device may also include other types of output devices such as speakers, for example. In some cases, device 12, 14 may include multiple of any one or more of processors, applications, software modules, second storage devices, network connections, input devices, output devices, and display devices.

Although devices 12, 14, 16, 18 are described with various components, one skilled in the art will appreciate that the devices 12, 14, 16, 18 may in some cases contain fewer, additional or different components. In addition, although aspects of an implementation of the devices 12, 14, 16, 18 may be described as being stored in memory, one skilled in the art will appreciate that these aspects can also be stored on or read from other types of computer program products or computer-readable media, such as secondary storage devices, including hard disks, floppy disks, CDs, or DVDs; a carrier wave from the Internet or other network; or other forms of RAM or ROM. The computer-readable media may include instructions for controlling the devices 12, 14, 16, 18 and/or processor to perform a particular method.

Devices such as server platforms 12, 16 and devices 14, 18 can be described performing certain acts. It will be appreciated that any one or more of these devices may perform an act automatically or in response to an interaction by a user of that device. That is, the user of the device may manipulate one or more input devices (e.g. a touchscreen, a mouse, or a button) causing the device to perform the described act. In many cases, this aspect may not be described below, but it will be understood.

As an example, it is described below that the devices 14, 16, 18 may send information to the server platform 12. For example, a user using the device 14 may manipulate one or more inputs (e.g. a mouse and a keyboard) to interact with a user interface displayed on a display of the device 14. Generally, the device may receive a user interface from the network 20 (e.g. in the form of a webpage). Alternatively, or in addition, a user interface may be stored locally at a device (e.g. a cache of a webpage or a mobile application).

Server platform 12 may be configured to receive a plurality of information, from each of the plurality of devices 14, 16, 18.

In response to receiving information, the server platform 12 may store the information in storage database. The storage may correspond with secondary storage of the devices 14, 16, 18. Generally, the storage database may be any suitable storage device such as a hard disk drive, a solid-state drive, a memory card, or a disk (e.g. CD, DVD, or Blu-ray etc.). Also, the storage database may be locally connected with server platform 12. In some cases, storage database may be located remotely from server platform 12 and accessible to server platform 12 across a network for example. In some cases, storage database may comprise one or more storage devices located at a networked cloud storage provider.

Figure 2:
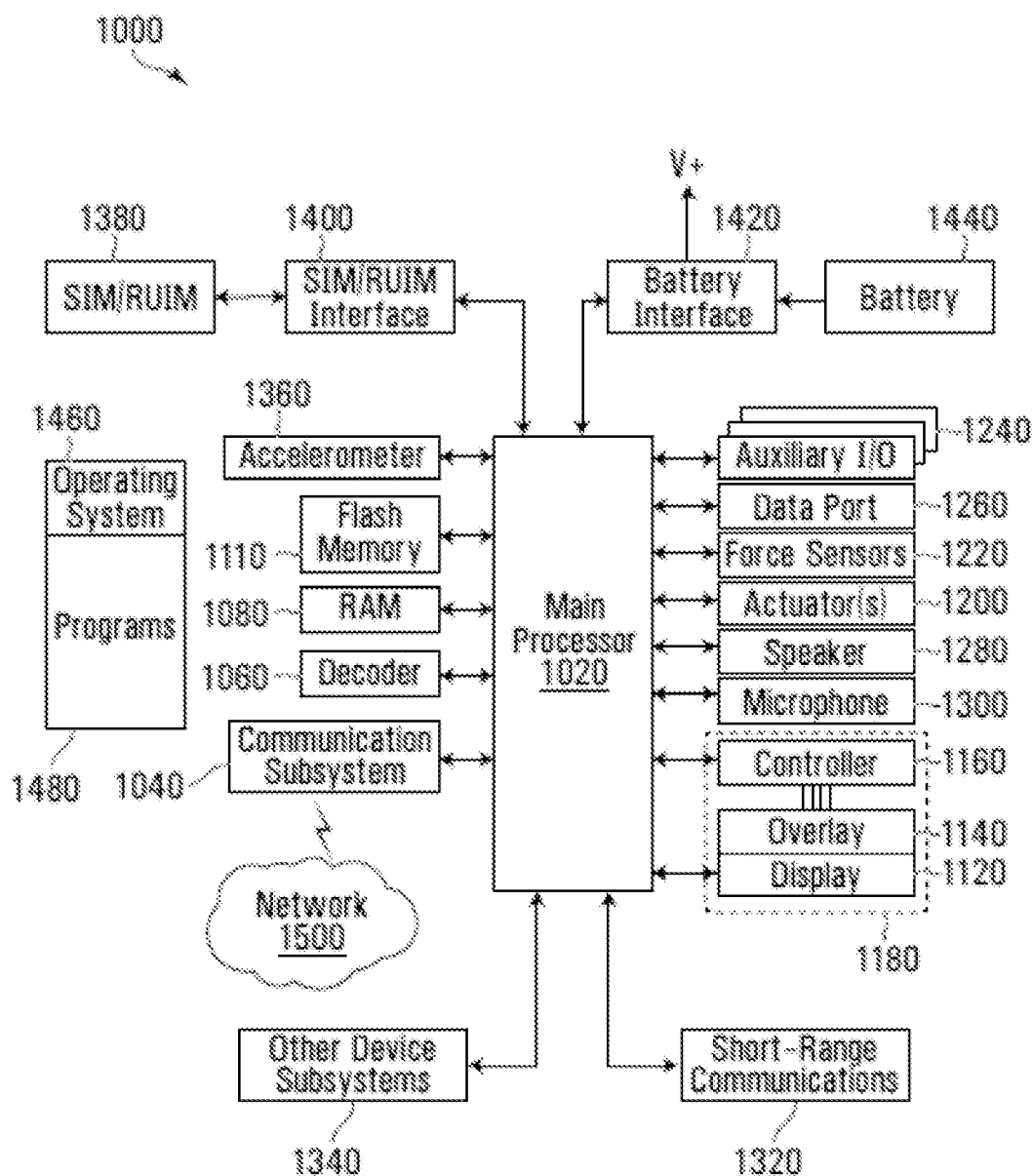
FIG. 2 is a block diagram of a computing device of FIG. 2.

Referring now to FIG. 2, shown therein is a block diagram of components of a computing device 1000 for use in the system 10 of FIG. 2, according to an embodiment. For example, the device 1000 may be the electronic progress notes server 12 of FIG. 2.

The device 1000 may be any suitable computing device such as a tablet, a smartphone, a desktop, a workstation, a server, etc. The device 1000 includes multiple components such as a processor 1020 that controls the operations of the device 1000. Communication functions, including data communications, voice communications, or both may be performed through a communication subsystem 1040. Data received by the device 1000 may be decompressed and decrypted by a decoder 1060. The communication subsystem 1040 may receive messages from and send messages to a wireless network 1500.

The wireless network 1500 may be any type of wireless network, including, but not limited to, data-centric wireless networks, voice-centric wireless networks, and dual-mode networks that support both voice and data communications.

The device 1000 may be a battery-powered device and as shown includes a battery interface 1420 for receiving one or more rechargeable batteries 1440.

The processor 1020 also interacts with additional subsystems such as a Random Access Memory (RAM) 1080, a flash memory 1100, a display 1120 (e.g. with a touch-sensitive overlay 1140 connected to an electronic controller 1160 that together comprise a touch-sensitive display 1180), an actuator assembly 1200, one or more optional force sensors 1220, an auxiliary input/output (I/O) subsystem 1240, a data port 1260, a speaker 1280, a microphone 1300, short-range communications systems 1320 and other device subsystems 1340.

In some embodiments, user-interaction with the graphical user interface may be performed through the touch-sensitive overlay 1140. The processor 1020 may interact with the touch-sensitive overlay 1140 via the electronic controller 1160. Information, such as text, characters, symbols, images, icons, and other items that may be displayed or rendered on a portable electronic device generated by the processor 102 may be displayed on the touch-sensitive display 118.

Figure 3:
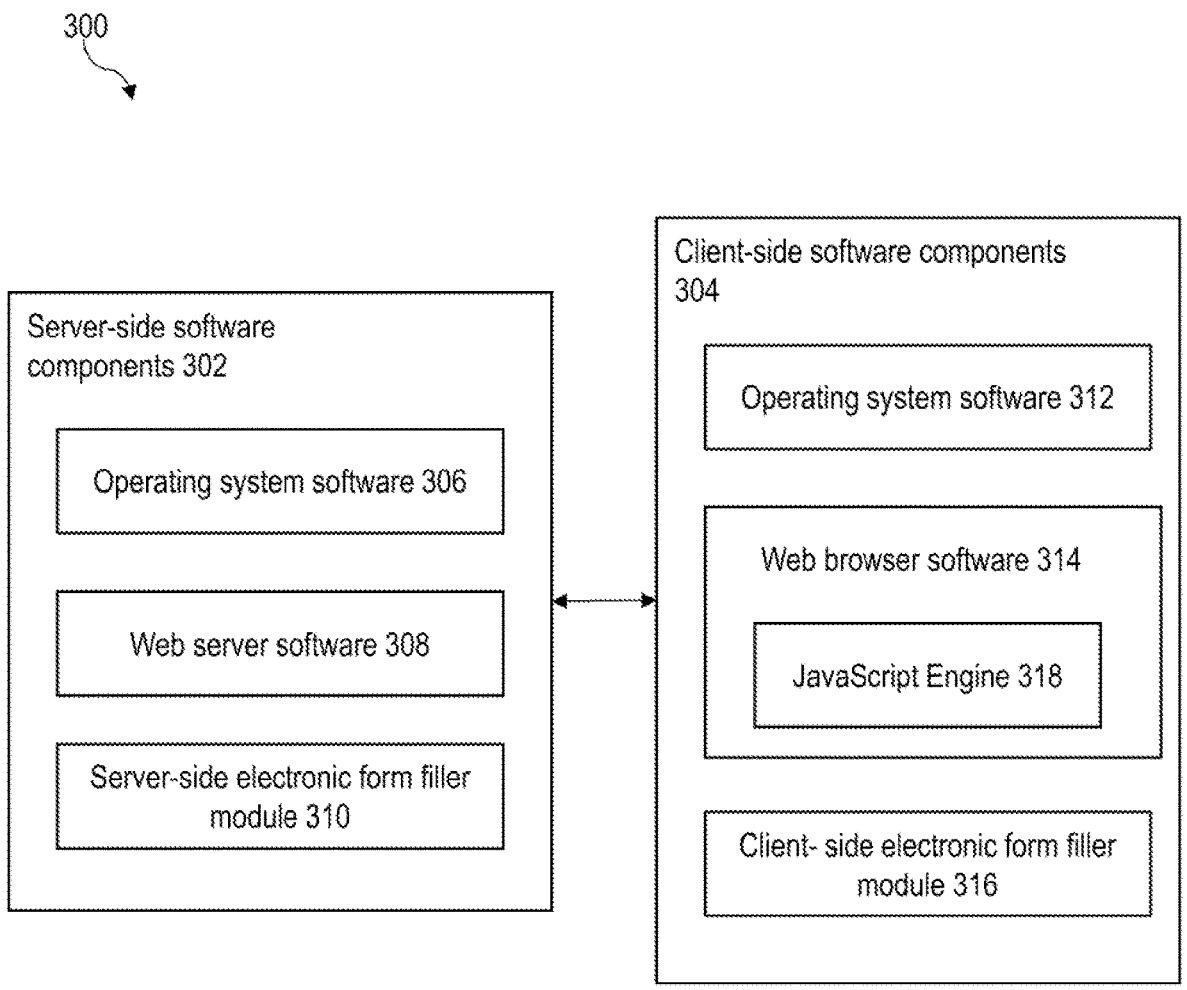
FIG. 3 is a block diagram of software components of a computer system for electronic forms, according to an embodiment.

The processor 1020 may also interact with an accelerometer 1360 as shown in FIG. 3. The accelerometer 1360 may be utilized for detecting direction of gravitational forces or gravity-induced reaction forces.

To identify a subscriber for network access according to the present embodiment, the device 1000 may use a Subscriber Identity Module or a Removable User Identity Module (SIM/RUIM) card 1380 inserted into a SIM/RUIM interface 1400 for communication with a network (such as the wireless network 1500). Alternatively, user identification information may be programmed into the flash memory 1100 or performed using other techniques.

The device 1000 also includes an operating system 1460 and software components 1480 that are executed by the processor 1020 and which may be stored in a persistent data storage device such as the flash memory 1100. Additional applications may be loaded onto the device 1000 through the wireless network 1500, the auxiliary I/O subsystem 1240, the data port 1260, the short-range communications subsystem 1320, or any other suitable device subsystem 1340.

For example, in use, a received signal such as a text message, an e-mail message, web page download, or other data may be processed by the communication subsystem 1040 and input to the processor 1020. The processor 1020 then processes the received signal for output to the display 1120 or alternatively to the auxiliary I/O subsystem 1240. A subscriber may also compose data items, such as e-mail messages, for example, which may be transmitted over the wireless network 1500 through the communication subsystem 1040.

For voice communications, the overall operation of the portable electronic device 1000 may be similar. The speaker 1280 may output audible information converted from electrical signals, and the microphone 1300 may convert audible information into electrical signals for processing.

Referring now the FIG. 3, shown therein is a simplified organization of software components 300 of the system 10 of FIG. 1, according to an embodiment.

The software components 300 may be stored within memory 1080 of server 12 and end user device 16, respectively.

The software components 300 include server-side software components 302 and client-side software components 304. The server software components 302 may be stored in memory 1080 of server 12. The client software components 304 may be stored in memory 1080 of end user device 16. The server-side components 302 and client-side components 304 may communicate with each other in order to provide various features and functionalities of the systems and methods described herein.

The server software components 302 include an operating system software 306, a web server software 308, and a server-side electronic form filler module 310.

The operating system (OS) software 306 may be, for example, Microsoft Windows, Linux, Macintosh OSX, UNIX, or the like. The OS software 306 allows the web server software 308 to access one or more processors 1020, network interface 1040, persistent storage 1110, memory 1080, and one or more I/O interfaces 1240 of the server 12.

The OS software 306 includes a networking stack such as, for example a TCP/IP stack, allowing the server 12 to communicate with end-user computing devices 14, 16, 18 through network interface 1040 using a protocol such as TCP/IP.

The web server software 308 may be, for example, Apache, Microsoft Internet Information Services (IIS), or the like.

The server-side electronic form filler module 310 includes software components including instructions used in storing, rendering, and manipulation of electronic data entry forms that execute on one or more processors 1020 of the server 12. The electronic data entry forms may include one or more form types. Form types may include healthcare-related forms such as progress notes and other clinical forms. In another example, the electronic form may be an order set form. The electronic form includes a plurality of data entry fields which, in the context of a healthcare form, may receive input data from a user about a patient.

The server-side electronic form filler module 310 may, for example, store and retrieve declarative definitions of electronic forms from secondary storage. The server-side electronic form filler module 310, when executed, may cooperate with corresponding client-side components (i.e. executing on one or more processors 1020 of an end user computing device 16) to allow a user device 14 to render forms and receive user input for manipulating and providing input data to rendered forms.

The client-side software components 304 include an operating system software 312, a web browser 314, and a client-side electronic form filler module 316.

The OS software 312 may be, for example, Microsoft Windows, iOS, Android, or the like. The OS software 312 allows the web browser 314 to access one or more processors 1020, network interface 1040, persistent storage 1110, memory 1080, and one or more I/O interfaces 1240 of end user computing device 16.

The web browser 314 may be, for example, Google Chrome, Chromium, Mozilla Firefox, Apple Safari, Microsoft Internet Explorer, Microsoft Edge, or the like. The web browser 314 enables end user computing device 16 to retrieve and render web pages such as may be accessed using network interface 1040 of end user computing device 16.

The web browser 314 includes a JavaScript engine 318. The JavaScript engine 318 is responsible for executing JavaScript code such as may be retrieved by or included in one or more of the aforementioned web pages. For example, the JavaScript engine 318 may execute JavaScript code in a web page and/or one or more JavaScript code libraries referenced therein.

The client-side electronic form filler module 316 includes software components including instructions used in rendering and manipulation of electronic data entry forms that execute on one or more processors 1020 of end user computing device 16.

In some embodiments, the client-side electronic form filler module 316 may include JavaScript code that is executed by the JavaScript engine 318. The client-side electronic form filler module 316, when executed, may cooperate with the server-side electronic form filler module 310 executing on server 12 to allow the end user device 14 to render forms and receive user input for manipulating and providing input data (such as clinical data) to rendered forms.

In an embodiment, data (such as clinical data inputted to the form) may be transmitted between the server 12 and the end user device 16 using a lightweight data exchange format. The lightweight data exchange format may be JavaScript Object Notation (JSON).

The lightweight data exchange format may be used to exchange data between a browser (e.g. on end user device 16) and a server (e.g. server 12) where the system 10 uses a web-based application.

In an example using JSON, at the server 12 a JavaScript object may be converted into JSON and the JSON sent to the browser. The JSON received at the browser from the server 12 may be converted into JavaScript objects. For example, progress note data comprising data inputted into a progress note form may be stored in a JavaScript object at the user device 16. The object is converted into JSON and the JSON is transmitted to the server 12. The progress note data is received from the device 16 at the server 12 in JSON format. The JSON may be converted into a JavaScript object.

Figure 4:
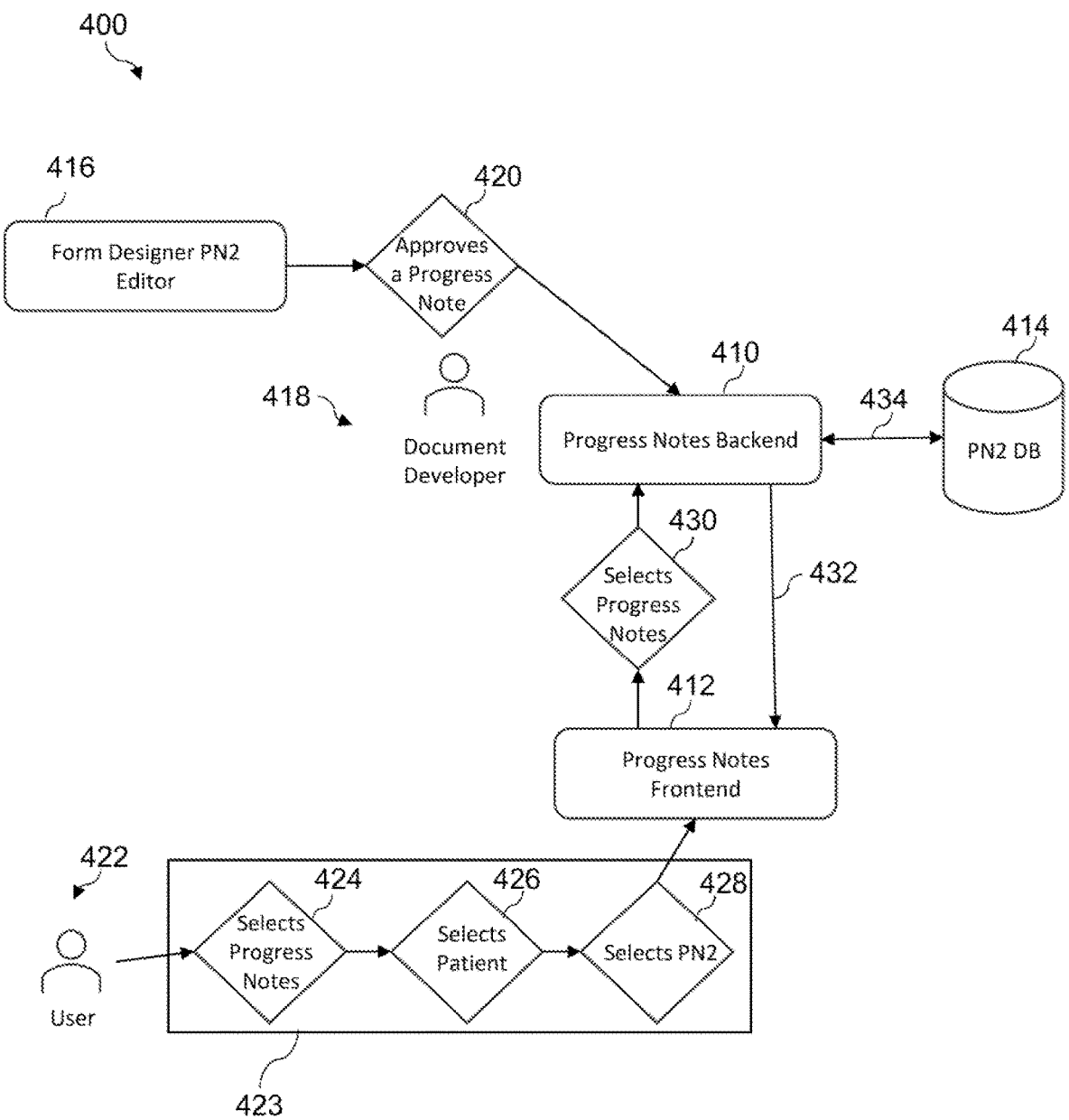
FIG. 4 is a block diagram of a computer system for processing electronic clinical notes, according to an embodiment.

Referring now to FIG. 4, shown therein is a computer system 400 for electronic progress notes, according to an embodiment. While examples and embodiments will be described with reference to a progress note form type, it is understood that such examples and embodiments can be applied to other electronic form types and in particular to electronic healthcare form types where historical data, such as patient data inputted to the form at a previous time, may need to be saved in order to provide proper context to the form viewer and to provide effective care.

The system 400 includes a progress notes backend 410 (e.g. server-side progress notes module 310 of FIG. 3) and a progress notes frontend 412 (e.g. client-side progress notes module 316 of FIG. 3). The progress notes backend 410 may be implemented at the form management server 12. The progress notes frontend 412 may be implemented at the user device 16.

The progress notes backend 410 and frontend 412 may operate together as a web-based application.

The system 400 includes a progress notes database 414. The progress notes database 414 is in communication with the progress notes backend 410. The progress notes database 414 may be stored at the form management server 12 or at another server communicatively connected to the form management server (e.g. via network 20), such as a database server.

The progress notes database 414 stores progress notes data. The progress notes data may include progress note form template data (or "template data" or "template") and progress notes input data ("form data", "input data" or "clinical data").

The form template data includes a progress note form template which includes a plurality of relevant information regarding a patient and mimic an unfilled or uncompleted clinical progress note.

The progress note template data may be generated in response to a user, such as a form designer or document developer, interacting with a form designer application (e.g. form designer application 416 below).

The input data includes patient or other clinical information provided by a user, such as a clinician. The input data is generated in response to a user input received at the client device 16 using the progress notes frontend 412. For example, the input data may correspond to data inputted by a user to a data entry field in the form.

The system 400 includes a form designer application 416. The form designer application 416 is a software application for designing and editing computerized electronic data-entry forms. The form designer application 416 may include a progress note editor module, which may be a specially adapted software component or module of the form designer application 416 for building progress note form templates.

The form designer application 416 may be configured to generate a JSON document (or other web-based document) defining an electronic form. In particular, the form designer application 416 may include an editor having a user interface which allows a user to create a visual representation of the electronic form, such as by dragging and dropping form components or elements onto a form design area. The editor is configured to generate the JSON document representing the visual representation.

In an embodiment, the form designer application 416 can be used to generate an electronic data entry form that is defined in a declarative format. For example, the form may be modeled as a hierarchy (or hierarchical model) of user-interface element definitions. The form can be rendered based on the hierarchical model. The form designer application 416 may include an editor that allows a user to view a rendering of such an electronic data entry form definition. The user may then modify the form, such as by adding or deleting elements. For example, a user may drag-and-drop a user interface element from a palette onto the rendered form in order to add the element to the form.

Electronic data entry forms can be defined in a declarative format. For example, the form may be modeled as a hierarchy of user-interface element definitions. The form can then be rendered based on the hierarchical model. An editor can be provided (e.g. form designer application 416) that allows a user to view a rendering of such an electronic data entry form definition. The user (e.g. document developer 418, described below) may then modify the form such as by adding or deleting elements. For example, a user may drag-and-drop a user interface element from a palette onto the rendered form in order to add the element to the form.

The hierarchical model may then be modified to represent the addition of the element. For example, it may be necessary to determine where in the hierarchical model to insert a user-interface element definition corresponding to an added user-interface element.

Once the element is added, the form can then be re-rendered to reflect the added element.

As described, an electronic form, such as an electronic progress note or other healthcare form, can be defined using a declarative definition. In an example embodiment, an electronic progress note can be defined using a nested (i.e. hierarchical) JavaScript data structure expressed in JavaScript Object Notation (JSON). The above JSON format can be used to define a form such as, for example, a clinical note form.

A form definition (or a definition of a page thereof) can include definitions of both relative and floating components. Relative components are components that are automatically laid out on the form page, relative to one another. Floating components are components that have a specified x-y location of the form page.

Relative components may include module components (used for grouping user-interface components in areas of the form) and text components (used for labelling areas of the form).

A module component includes a variety of metadata entries regarding the module including, for example, date stamps for tracking changes and various identifiers for the component.

Notably, the module component includes a collection of content blocks (described below) that are nested inside that module.

A text component includes a variety of metadata regarding the text component including, for example, date stamps for tracking changes and various identifiers for the component.

Notably, the text component includes the text string associated with the Text Component that will be displayed on the form.

Module components include a collection of content blocks. Notably, a content block acts as a container for nested components, namely form components, module components and additional text components.

A content block also includes a variety of metadata regarding the content block including, for example, date stamps for tracking changes and various identifiers for the component.

A form component acts as a container for both further content blocks and for field rows. A form component also includes a variety of metadata regarding the form component including, for example, date stamps for tracking changes and various identifiers for the component.

A field row represents a row within a given form component. In addition to the various metadata elements typical to most components, the field row includes a collection of row elements.

Row elements is a category that includes various user-interface components. A row element is a visual UI component that can be rendered out in a horizontal fashion (although wrapping as necessary given the horizontal space on the page), each of which is rendered out in the order that they are present in the field rows. There may be many types of row elements but they are unified in concept by their fact that they are rendered out in order, and a grouping of them established a field row.

One possible row element is a label which displays text. Another possible row element is a checkbox. Another possible row element is a radio button. Another possible row element is a textbox which provides a place for entering a line of text. Another possible row element is a text area which provides a place for entering multiple lines of text. Another possible row element is a mandatory checkbox which requires entry of a checkmark. Another possible row element is a text area for the mandatory check box. Another possible row element is a signature area which provides a place for entering multiple lines of text. Another possible row element is a barcode which provides a place for entering multiple lines of text. Another possible row element is a drop down (also known as a combo box) which allows a user to select amongst a number of options.

A form may also include floating components.

Notably both content blocks and field rows are meta-components used only in controlling the positioning of the other elements. For instance, in an example embodiment, form components may be arranged horizontally by default, whereas content blocks may be arranged vertically. Notably, however, neither content blocks nor field rows are displayed to a user directly.

A form component acts as a container for both further content blocks and for field rows. A form component also includes a variety of metadata regarding the form component including, for example, date stamps for tracking changes and various identifiers for the component. A field row represents a row within a given form component. In addition to the various metadata elements typical to most components, the field row may include a collection of row elements. As will become apparent row elements is a category that includes various user-interface components. A row element is a visual UI component that can be rendered out in a horizontal fashion (although wrapping as necessary given the horizontal space on the page), each of which is rendered out in the order that they are present in the field rows. There may be many types of row elements, and their various descriptions follow, but they are unified in concept by their fact that they are rendered out in order, and a grouping of them established a field row.

A form may include a data pull field. The data pull field may be added to the form using the form designer application (e.g. application 902 of FIG. 9). The data pull field is configured to pull data into the form from an existing data feed. The data pull field may be used to autopopulate certain fields directly using the data feed rather than filling out the field manually by the user. The data pull field may be a read only form element that can be prefilled with the data from the data feed. In an example, the data may be pulled from an application entry point (such as described below).

In some cases, any text field in the form may have rich text support.

As further described herein, in some embodiments, form elements may include condition visibility functionality in which visibility of at least a first form element (i.e. whether the first form element is displayed on the form) may be controlled based on a value input to a second form element (e.g. a conditional visibility controlling data entry field). In some cases, conditional visibility functionality may be implemented as a type of metadata that is a link from one form element to the value selected in another form element on the form. Metadata information that could be included for each module (and any form components located therein) may include data that links the rendering of this module on the form (and, potentially, the order on the page where it is rendered) to a certain value selected from a different form element that has already been placed on the form (e.g. a dropdown list or checkbox or radio button). In this way, by selecting a certain value in the dropdown list or checkbox/radio button (or other data entry field type), different modules will render on the form (and some may not). Further, the order in which the dropdown lists are selected can be used to control the order in which the modules are rendered, allowing the form-filler the ability to define which modules appear on a page, and in which order.

Referring still to FIG. 4, the form designer application 416 may include server-side and client-side software components. Server-side software components and client-side software components are software components including instructions used in rendering and manipulation of electronic data entry forms that execute on one or more processors 1020 of server 16 and client device 18, respectively.

The server-side software components may store and retrieve declarative definitions of forms from secondary storage.

The client-side software components may include JavaScript code that is executed by a JavaScript Engine.

The server-side software components, when executed, may co-operate with corresponding client-side components (i.e. executing on one or more processors 1020 of a client device 18) to allow a user device 14 to render forms and receive user input for manipulating rendered forms.

A document developer 418 may interact with the form designer 416 application, for example via client-side software components, at the client device 18. In doing so, the document developer 418 can create and edit an electronic progress note template. The created or edited template is stored in the system 400 as template data.

The form designer application 416 may include a form approval module. The form approval module is configured to allow the document developer 418 to view and approve a progress note or other electronic form template. Approval may amount to confirming the appearance and/or function of the electronic form and its suitability for use. An example of such approval is shown at 420.

In an embodiment, the form approval module may operate such that the document developer 418 can provide an input via a user interface of the form designer application 416 presented at the client device 18 indicating approval of the progress note form template. Upon receiving the approval indication, the form designer application 416 communicates with the progress notes backend 410, for example via the server-side software components of the form designer application 416. The progress notes backend 410 may then receive the approved form template (e.g. in JSON or other web-based document format) and store the form template in the progress notes database 414.

A user 422, such as a healthcare professional (e.g. doctor, nurse, etc.), interacts with the system 400 via a user interface 423 presented at the user device 16. The user interface may be a component of a generic electronic medical record application or may be a component of a progress notes-specific application. Regardless of the implementation, the user interface facilitates communication with and data input to the progress notes frontend 412.

At 424, the user 422 visits an application entry point ("EP") via the user interface.

The EP may be an application that holds other applications inside of it. The EP may be configured to receive various user input data, such as patient selection data indicating a selected patient. In an embodiment, after selecting the patient, the EP may generate and display a selectable tab or the like that, when selected by the user, launches the progress notes application. In other embodiments, applications other than the EP may be used (i.e. the progress note application can live inside of a different application). The progress note application may rely on the EP to provide the patient data that may be used to generate the progress note. The EP may be used to login to the progress note application. In other embodiments, the progress note application may live on its own (without the EP) and store its own patient data. In such embodiments, the progress note application may include a user interface component configured to provide a menu or the like from which a user can select a patient for which a new or updated progress note can be created (or an existing progress note can be viewed). In some embodiments, the progress notes application may be implemented as a service and not live inside a different application. For example, the progress notes application may be called, as a service, through the use of one or more API endpoints where specific API calls are made to result in certain form modifications, for template modifications, or to return a specific form template, form data set, fully rendered form, or set of form rendering instructions.

At 426, upon visiting the EP, the user 422 is presented with a user interface allowing the user 422 to select a patient by providing a patient selection data input at the user device 16.

At 428, upon selecting the patient, the user 422 is presented with a user interface allowing the user 422 to select a "progress note" option by providing a progress note selection data input at the user device 16.

In cases where the system 400 stores multiple types of progress note form templates (e.g. for use in different contexts, by different departments, etc.), the progress note selection data provided at 428 may include a form type indication specifying which of the plurality of progress note form-types the user wishes to use.

The user interfaces presented at 424, 426, 428 may be a single user interface or multiple user interfaces.

The patient selection data and progress note selection data provided at 426 and 428, respectively, are communicated via the user interface 423 to the progress notes frontend 412.

At 430, the progress notes frontend 412 communicates the progress note selection data and patient selection data to the progress notes backend 410. In an embodiment, the frontend 412 and backend 410 are communicatively connected via a computer network (e.g. Internet).

At 432, the progress notes backend 410 uses the received selection data to retrieve certain data from the progress notes database 414.

Retrieved data may include progress note form template data (corresponding to the progress note selection) and progress note input data (form data).

Progress note input data includes clinical data input into the progress note form, for example via one or more data input fields. Clinical data may include any patient-specific data.

Accordingly, in a first instance of use with a patient, the progress notes backend 410 may retrieve only the form template as the system 400 (progress notes database 414) is not storing any progress note input data for the patient.

After progress note input data has been received, whether during a first use or subsequent use of the progress note form, the progress note backend 410 receives clinical data from the database 414 in addition to the form template data.

At 434, the progress notes backend 410 provides the retrieved data to the progress notes frontend 412 for rendering of the electronic progress note. As previously described, the retrieved data includes form template data and may include progress note input data.

In providing the retrieved data to the progress notes frontend 412, the progress notes backend 410 may be configured to send the retrieved data in a web-based format from the server 12 to the user device 16. The web-based format may be a lightweight data exchange format such as JSON. In some cases, the progress notes backend 410 is configured to convert the retrieved data or a portion thereof to the web-based format prior to transmitting the data.

Though not shown, the user 418 can provide input data at user device 16 via one or more input fields in the rendered progress note, which may then be received by the progress notes frontend 412, communicated from the frontend 412 to the progress notes backend 410, and then passed from the backend 410 to the database 414 for storage.

Figure 5:
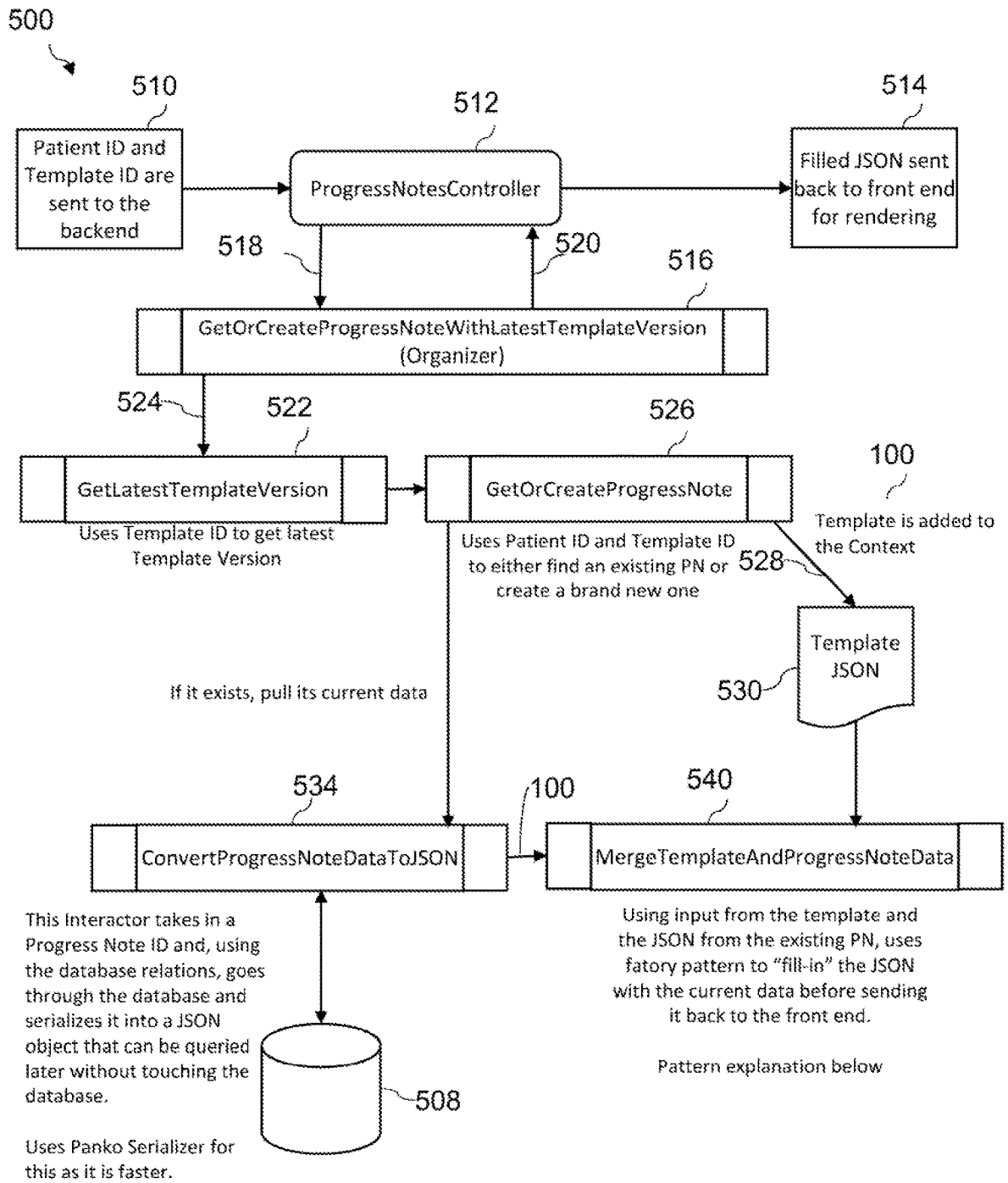
FIG. 5 is a flow diagram illustrating a workflow for creating a filled JSON implemented by the progress notes backend software component of FIG. 3, according to an embodiment.

Referring now to FIG. 5, shown therein is a computer-implemented workflow 500 for creating a filled JSON, according to an embodiment.

The workflow 500 may be implemented by the system 400 of FIG. 4, and in particular, by the progress notes backend software component 410.

The workflow 500 may be invoked/triggered by the system 400 at 430 of FIG. 4. For example, the progress notes backend 410 may implement the workflow 500 upon receiving input selection data (e.g. patient selection data and template selection data) from the progress notes frontend software component 412.

At 510, patient ID data and template ID data are sent to the progress notes backend 410. The patient ID and template ID data are received from the progress notes frontend 412.

The progress notes backend 410 includes a progress notes controller 512. The progress notes controller 512 is a software component which manages or directs the flow of data in the backend 410. The controller 512 may be located at processor 1080 of server 12.

The progress notes backend 410 also includes or is otherwise in communication with a database 508. The database 508 stores progress note data. The database 508 may be database 414 of FIG. 4.

The progress notes controller 512 is configured to receive the patient ID data and template ID data at 510 and, after processing by the backend 410, send a filled JSON (or other web-based document, as the case may be) at 514 to the progress notes frontend software component 412. The filled JSON can be used by the frontend 412 to render an electronic progress note in a user interface provided at the user device 16.

The progress notes backend 410 includes a get or create function 516. The get or create function 516 may be called by the progress notes controller 512 upon receipt by the controller 512 of the patient and template ID data at 510.

The get or create module 516 is configured to receive data at 518, get or create an electronic progress note with the latest template version using the received data, and return the retrieved or created progress note with the latest template version at 520. The data returned at 520 may be sent to the frontend 412 at 514 by the controller 512 to be used in electronic form rendering.

The progress notes backend 410 includes a get latest template version function 522. The get latest template version function 522 may be called by the get or create function 516 at 524.

The get latest template version function 522 is configured to receive and use the template ID data received by the controller 512 at 510 to retrieve form template data representing an electronic form template. The retrieved template data may represent the latest template version (i.e. the most current or recent version of the form template. The form template data may be stored in the database 508.

The progress notes backend 410 includes a get or create progress note function 526. The get or create progress note function 526 may be called by the get latest template version function 522. The get or create progress note function 526 is configured to use the patient ID data and the template ID data to either find an existing progress note stored in the system (e.g. in database 508) or create a new progress note if no existing note exists. For example, a progress note may exist where a patient has already been assessed by a clinician for a particular visit or condition, whereas a progress note may need to be created where the patient has not yet been assessed.

If a progress note data exists (i.e. is stored in the system), the function 526 pulls current data for the progress note. Whether progress note data exists may be determined using the patient ID data and template ID data, which may be linked to or otherwise associated with progress note data stored in the database 508 such that the progress note data can be pulled or retrieved using the patient ID data and template ID data.

The get or create progress note function 526 adds the progress note template to the context in the get or create progress note at 528. The context may be the object where any data is put before it is returned to whatever called it. The get or create progress note function 526 can access the data on the context 528 (which, in this case, is the template data). The template data may be in JSON format or may be converted from a first data format to a template JSON format. The template JSON is illustrated at 530.

The progress notes backend 410 includes a convert progress note data to JSON function 534. The convert progress note data to JSON function 534 may be called by the get or create progress note function 526 during its execution.

The convert progress note data to JSON function 534 may be an interactor that is configured to take in progress note ID data and, using database relations, go through the database 508 and serialize progress note data, which is stored in the database 508 and associated with/linked to the progress note ID data, into a JSON object. The JSON object can be queried against later without touching the database 508. In an embodiment, the function 534 may use a Panko Serializer or the like, which may have the advantage of faster performance.

The progress notes backend 410 includes a merge template and progress note data function 540. The merge template and progress note data function 540 may be called by the convert progress note data to JSON function 534 during its execution.

The merge template and progress note data function 540 merges the template data and progress note data to generate a filled JSON form (or other web-based document). The filled JSON is sent to the frontend 412 at 514.

In an embodiment, the merge template and progress note data function 540 uses the template JSON data 530 (which has been added to the context at 528) and the JSON generated from the stored progress note data (generated by the function 534) to "fill in" the template JSON 530 with the current progress note data JSON before sending the filled JSON form back to the frontend 412. In doing so, the function 540 may use a factory pattern to fill in the JSON template with the current progress note data, such as factory pattern 600 described below in reference to FIG. 6.

Figure 6:
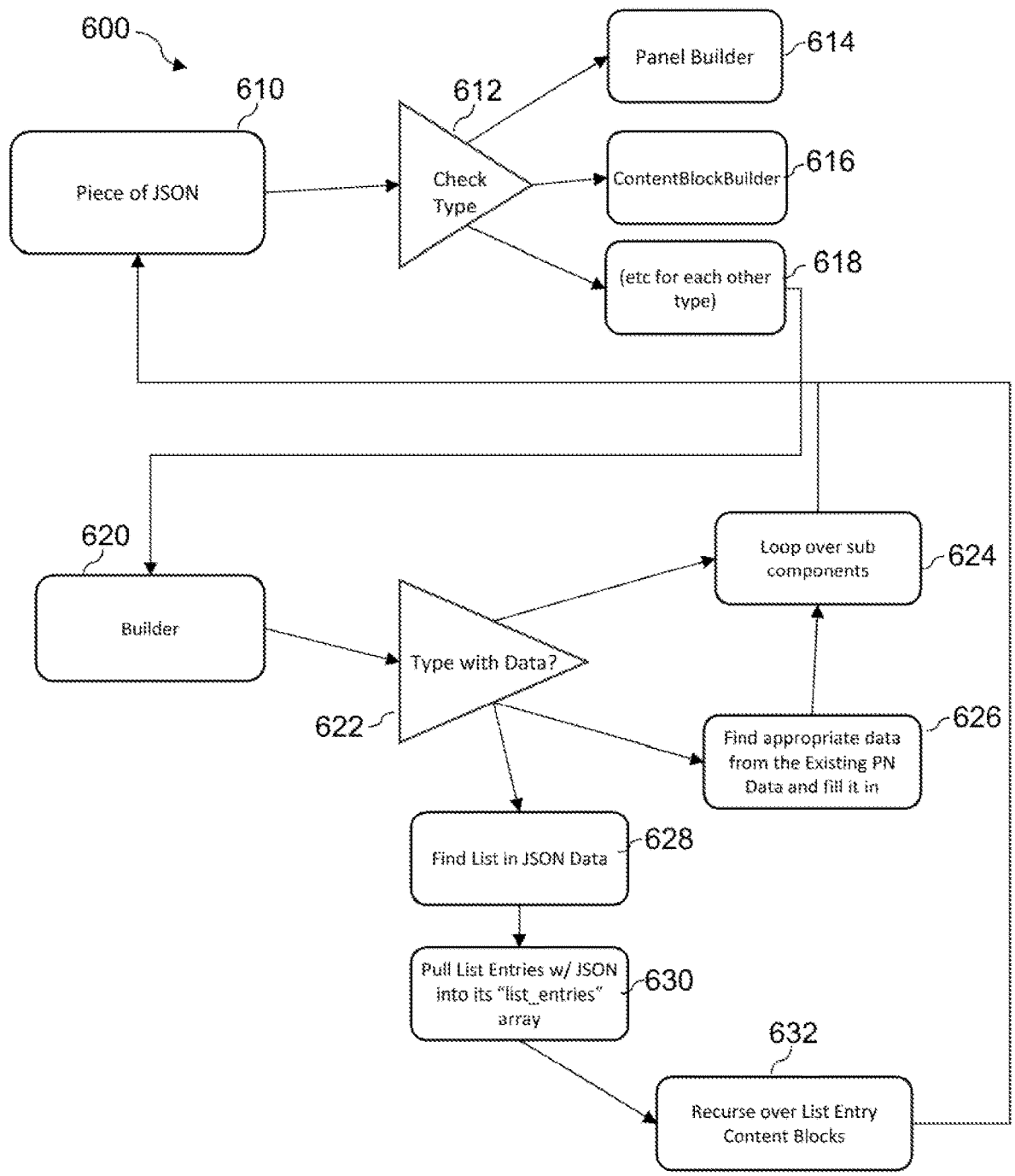
FIG. 6 is a flow diagram of a factory pattern component implemented by the progress notes backend software component of FIG. 3 as part of the workflow of FIG. 4, according to an embodiment.

Referring now to FIG. 6, shown therein is a factory pattern workflow 600 for filling in the JSON with the current data, according to an embodiment. For example, the factory pattern 600 may be implemented or otherwise invoked by the merge template and progress note data function 540 of FIG. 5. The workflow 600 is implemented in the merge template and progress note data function 540. The progress note template (form template) is the structure of the progress note. The progress note data (form data), which is patient-specific and used to fill out the progress note template to generate a progress note, is stored separately from the progress note template. The workflow 600 provides an embodiment of the recursive algorithm for filling or instantiating the progress note (which includes the progress note template filled with the progress note data).

The workflow 600 starts with a piece of JSON 610. The piece of JSON 610 is a component of the progress note template or structure of the progress note. In this sense, the workflow 600 may proceed through the JSON template in pieces, such as by starting at the topmost part of the template.

At 612, the factory pattern 600 performs a check type function. This includes checking, for a form element in the template, what element type corresponds to the form element. Form element types may include, for example, a panel, a content block, a row element, a list, a section, a form component, a list entry, or any element which can be present in the progress note. The form elements are the collection of elements which are usable to create the electronic form (i.e. depending on the design, a given form may include only a subset of the possible form element types). For example, the progress note or other electronic form may be composed of a plurality of different form elements having different functions and serving different purposes. Some form elements may be displayed directly to the user in the rendered form, while other form elements may not. Some form elements may be configured to receive user input data (i.e. to "fill out" or add data to the form), while other form elements may provide structural or organizational functions for the form, such as by organizing or structuring how form elements can be arranged on the form or how form elements are displayed to the user in a rendered version of the form. Certain form elements may be configured to contain other form element types.

Once the form element type is determined at 612, the workflow 600 initiates a builder function for the respective determined form element type. For example, if the form element type determined at 612 is a panel, the workflow 600 initiates a panel builder function 614. If the form element type determined at 612 is a content block, the workflow 600 initiates a content block builder function 616. If the form element type determined at 612 is another form element type, the workflow initiates a builder function for the respective form element type, which in FIG. 6 is represented by box 618 (e.g. a list builder function for a list form element type).

In an embodiment, the workflow 600 may start with a root form element of the template. For example, the root element may be a form element which is not inside of anything else (i.e. not inside of another form element) and the workflow 600 may initiate by identifying the root element. Depending on what form element type the root element is, the workflow 600 gets a different class or object that is configured to handle how that particular part of the progress note or form is built (e.g. builder functions 614, 616, 618). For example, if the root element is a panel, the workflow 600 initiates the panel builder function 614. Each builder component may be configured to fill data differently from that of other form element types (e.g. panel builder fills data differently than for a list element type, or a row element type, etc.). Once the appropriate builder component has been identified, the workflow 600 proceeds to merge the progress note data with the progress note structure (i.e. template). At 620 a type has been identified (from function at 612) and the builder function 620 corresponding to the determined element type is initiated (e.g. builder 620 may be panel builder 614 for a determined panel element type).

At 622, the workflow 600 performs a determination of whether the identified type is a type with data. If there is no data associated with the particular element type, no further action is required other than looking into the element's child elements (or "sub-components") and inside the children of those child elements and so on (by looping over subcomponents at 624). In other words, if the type identified is not a type with data, the workflow 600 proceeds to loop over sub-components of the element at 624. This includes proceeding to step 610 for a particular piece of JSON (i.e. corresponding to a sub-component), which is then run through the workflow 600.

If the identified type is a type with data, the workflow 600 distinguishes between a list type and a non-list type. List elements may include extra steps such as getting the list entries and filling the list entries in the template. With a list element, in contrast to some other elements, additions may be made to the structure of the progress note (i.e. the template). For example, if a list has list entries, those list entries may be added to the template.

If the identified type is a non-list type with data, the workflow 600 proceeds to find appropriate data from the existing progress note data (stored in the database 508) and fill the appropriate data in at 626. This includes merging the progress note data for the element with the template.

Once the appropriate data is found and used to fill in the template at 626, the workflow 600 proceeds to loop over sub-components at 624.

After looping over sub-components at 624, workflow 600 proceeds to step 610 for the piece of JSON corresponding to the identified sub-component and the piece of JSON is run through the workflow 600.

If the identified type is identified as a list at determination 622, the workflow 600 proceeds to find the list in the JSON data at 628.

At 630, the workflow 600 proceeds to pull list entries with JSON into its "list_entries" array.

At 632, the workflow 600 proceeds to recurse over list entry content blocks.

After recursion over list entry content blocks is performed at 632, the workflow 600 proceeds to the piece of JSON step at 610, at which a next piece of JSON can be run through the workflow 600.

Figure 7A:
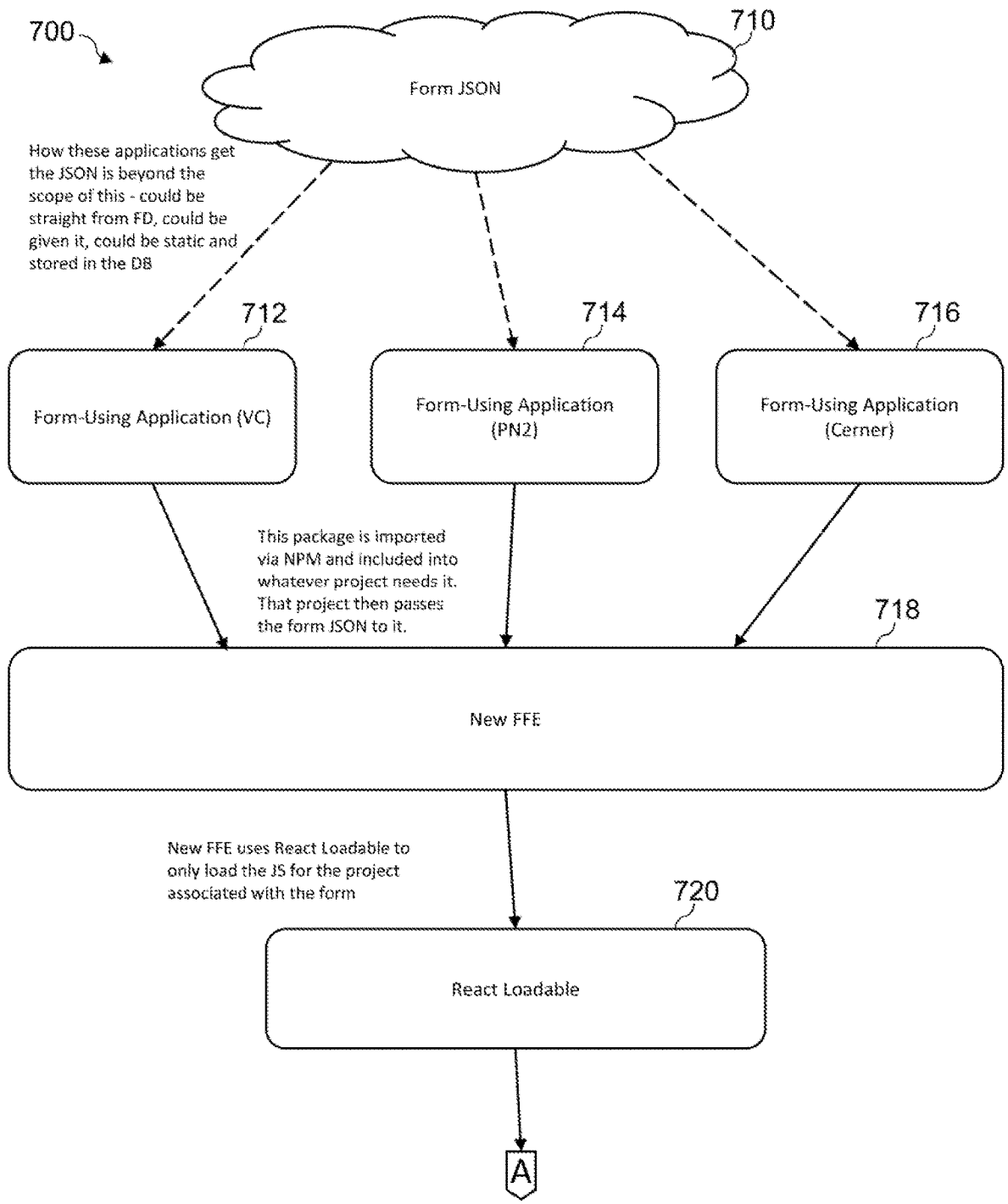
FIGS. 7A and 7B are a flow diagram of workflow implemented by a backend software component of a form management application, according to an embodiment.
Figure 7B:
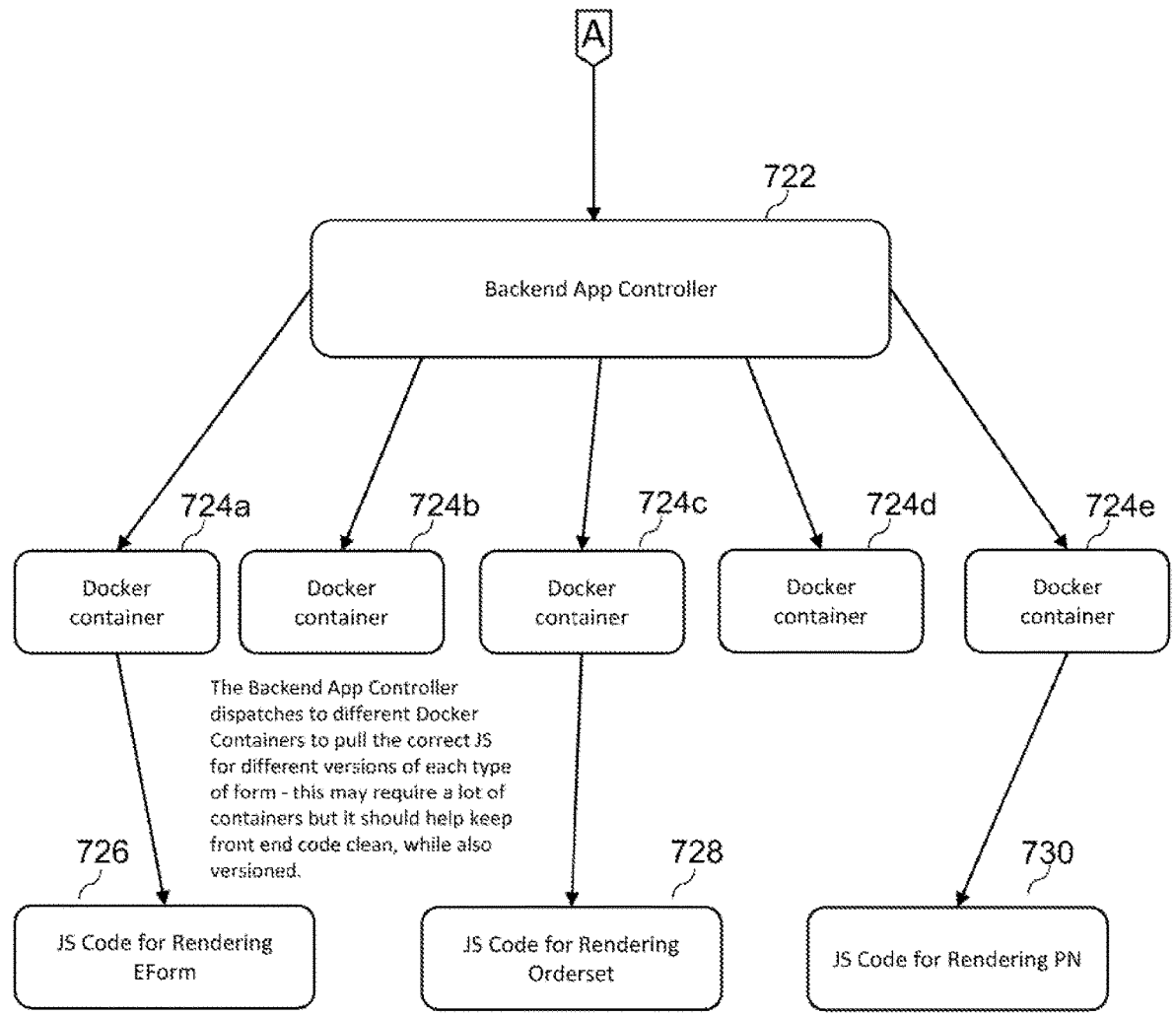

Referring now to FIGS. 7A and 7B, shown therein is an FFC workflow 700, according to an embodiment.

The workflow 700 may be implemented by the system 400 of FIG. 4, for example via the progress notes backend 410. The workflow 700, or a portion thereof, may be implemented at the server 12 of FIG. 1.

The workflow 700 starts with a form JSON 710. The form JSON may indicate what type of form it is. For example, the form JSON may indicate the form is a progress note form type (or other living or dynamic form type), an Eform type, or an Order Set form type, etc. The PN package or the backend can determine the form type based on the form type identification. Upon determining the form type is a progress note form type, the application returns the form template and the progress note package. The form filler engine uses the received progress note package to render the progress note form.

The form JSON may be provided to one or more formusing applications. A form-using application may be any application that is configured to present a user with an electronic fillable form to interact with. For example, the one or more form using applications may include a first form using application (VC) 712, a second form using application (progress notes) 714, and a third form using application (Cerner) 716. Each of the form using applications 712, 714, 716 . . . .

The form-using application may receive the form JSON 710 directly from a form designer application (e.g. form designer application 416 of FIG. 4), may be given the JSON, or the form JSON 710 may be static and stored in a database communicatively connected to the system implementing the form-using application (e.g. database 414 of FIG. 4).

The workflow 700 includes a form filler engine ("FFE") 718. The FFE 718 receives a package that is imported via a package manager (e.g. NPM) and included into whatever project needs the package. The project then passes the form JSON 710 to the FFE 718. The FFE 718 may function such that any application (e.g. applications 712, 714, 716) can use the FFE 718 to render the electronic form. The application passes a template JSON to the FFE 718, the FFE 718 calls a backend component to get a package that knows how to render the form based on what type of form it is.

The new FFE 718 uses React Loadable 720 to load only the JS for the project associated with the form 710.

The workflow 700 uses a backend app controller 722, which may be part of server-side software components 302 of FIG. 3 and may be implemented by server 12. The backend app controller 722 dispatches to a plurality of containers (e.g. Docker container) 724a to 724e to pull the correct JS code for different versions of each type of form. This may require a lot of containers, but should help keep front end code clean, while also versioned.

The server 12 stores JS code for rendering different versions of each form type (i.e. rendering logic for a given version of a particular form type). Form types may include, for example, any one or more of an EForm, an orderset, and a progress note. Accordingly, the server 12 stores JS code for rendering the EForm 726, JS code for rendering the orderset form 728, and JS code for rendering the progress note form 730.

In the case of FIGS. 7A and 7B, the backend app controller 722 dispatches to docker container 724a to pull the correct JS code for rendering the EForm 726. The backend controller 722 dispatches to container 724c to pull the correct JS code for rendering the orderset form 728. The backend controller 722 dispatches to container 724e to pull the correct JS code for rendering the progress note form 730.

The workflow 700 may provide advantages. For example, the workflow 700 may allow for versioning, can be used to load/pull different versions of rendering logic (e.g. JS code 726), and may allow for versioning of the rendering logic/code that is sent back by the system which may provide for interpreting older form templates without issues/loss of functioning. Using the workflow 700 may eliminate the need to build rendering engines for each form template.

Figure 8A:
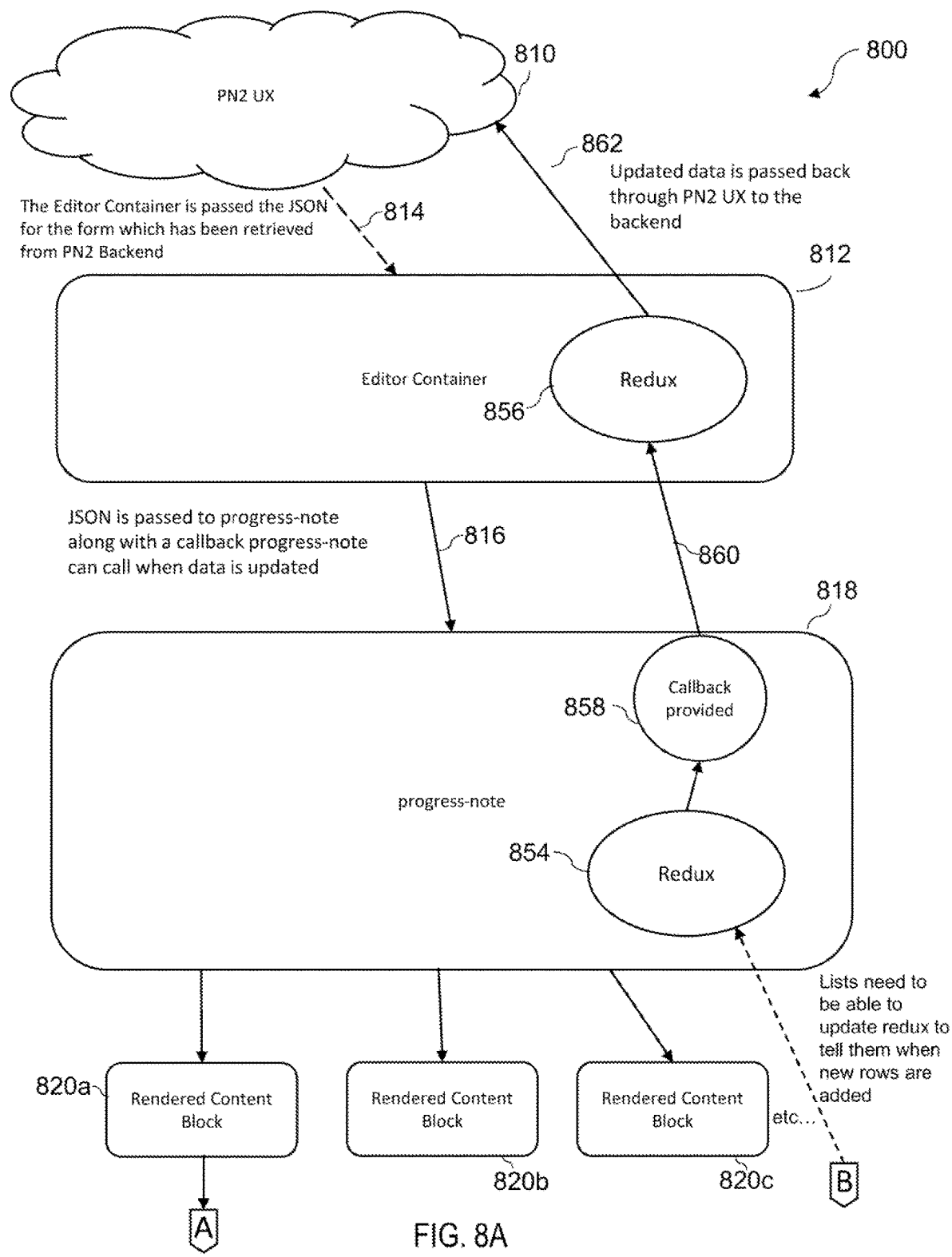
FIGS. 8A and 8B are a flow diagram of a workflow implemented by the progress notes frontend software component of FIG. 4, according to an embodiment.
Figure 8B:
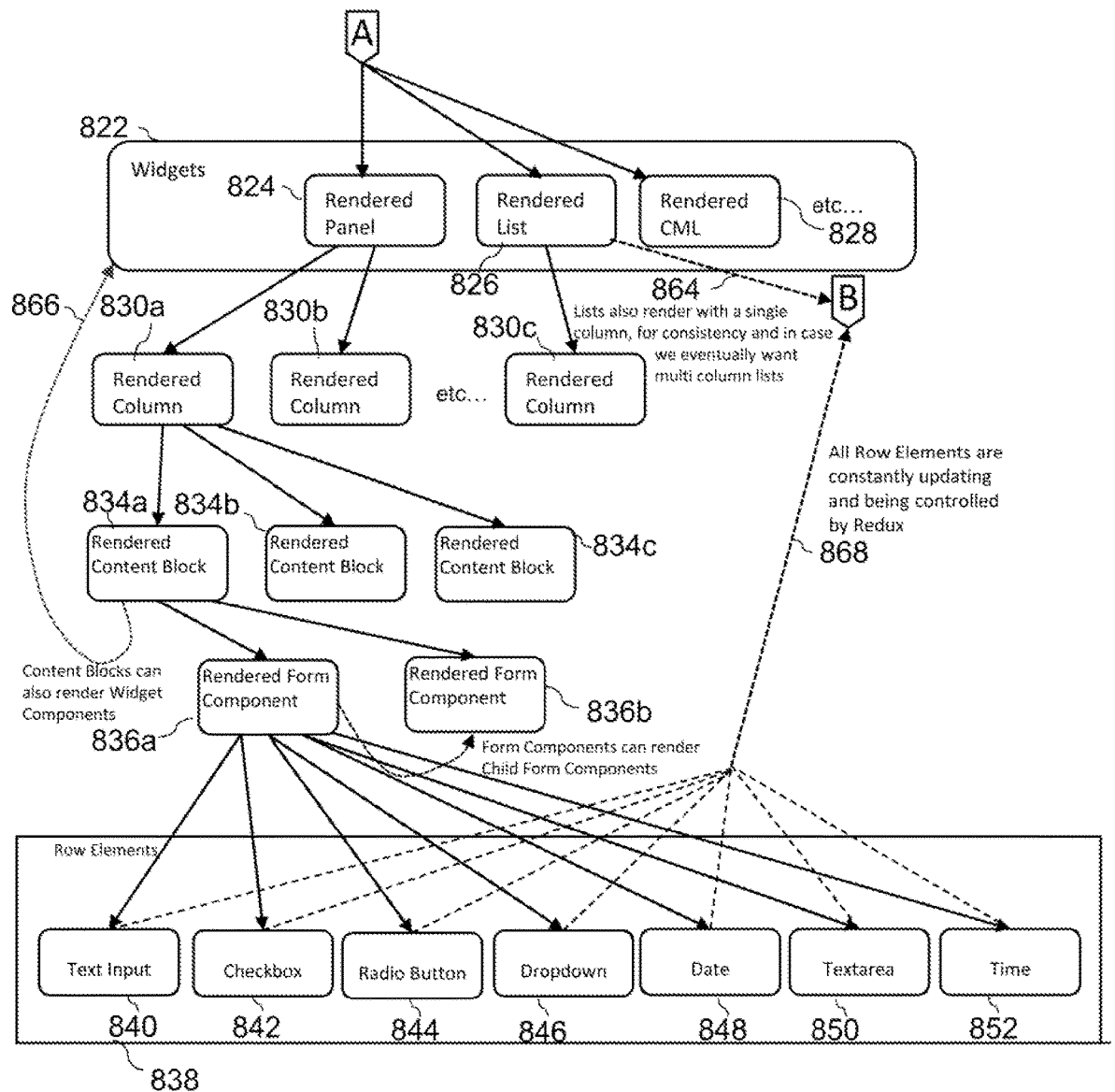

Referring now to FIGS. 8A and 8B, shown therein is a workflow 800 implemented by the progress notes frontend software component 412, according to an embodiment. The frontend software component includes a progress note application component ("PN app" or "PN2 UX") and a progress-note component ("progress note package" or "PN package"). The PN app is in communication with the PN package. In the embodiment of FIGS. 8A and 8B, the steps and components 810, 812, 814, 816, 856, and 862 are performed by or part of the PN app component. Steps and components 818-854, 858, and 860 are performed by or part of the PN package component.

Generally, the front-end component of the system is given a JSON template (progress note template) from the backend component. The PN template is passed, along with any progress note data (that has been previously entered into the form), into the PN app. The PN package component recurses through the entire template element by element to render the elements of the form. For example, the PN package may start with a content block component (e.g. 820a), which is an element that may contain other types of elements. For example, content block 820a may include a panel 824, a list 826, a rendered clinical module library ("CML") 828, etc. (collectively referred to as "widget components 822"). As each element is rendered, the workflow 800 continues through any child components (sub-components) of the element being rendered and renders those elements. For example, rendered panel 824 includes columns 830a, 830b and list 826 includes column 830c. Column 830a includes content blocks 834a, 834b, and 834c. The content block 834a may include one or more widget components 822, in which case rendering content block 834a (and similarly with content blocks 834b, 834c) causes the rendering of widget components 822 contained within the respective content block. The content block 834a also includes form components 836a and 836b. Rendering of form components, such as form component 836a, may result in the rendering of row elements 838 such as a text input 840, a checkbox 842, a radio button 844, a dropdown 846, a date entry 848, a text area 850, or a time entry 852. The row elements or form components may be any form element capable of and configured to receive input data from a user (i.e. parts of the form or note that can be filled out by the user).

The workflow 800 represents actions which may be performed by the frontend 412 once the form JSON is received from the backend 410 in order to display the progress note form to the user. The received JSON may include a form template which has been filled with progress note data according to the factory pattern 700 of FIGS. 7A and 7B.

The workflow 800 can be used to update a current JSON defining or representing the progress note. For example, when a user using the electronic form selects (i.e. checks) a checkbox on the electronic form, the workflow 800 can be used to update the JSON defining the electronic form to reflect the newly received input data (i.e. the checked checkbox). The workflow 800 can be used to similarly update the current JSON for the electronic progress note form upon receiving other forms of input data from a user via other data entry fields of the rendered form.

The workflow 800 starts at a progress notes UX 810, which is a component of the progress notes frontend 412.

The frontend 412 includes an editor container 812. The editor container 812 includes a redux component 856. The redux 856 may be a predictable state container for a JavaScript app. Redux 856 may make it easier to manage the state of an application. For example, the redux 856 may help manage the data displayed by the frontend 412 and how the frontend 412 responds to user actions.

At 814, the editor container 812 is passed the JSON for an electronic form that has been retrieved from the progress notes backend 410. For example, the JSON may have been retrieved by the backend 410 using the workflow 500 of FIG. 5.

At 816, the JSON is passed from the editor container 812 to a progress-note module 818. The progress-note module includes a redux component 854 and a callback 858. The JSON is passed along with the callback 858 which the progress-note module 818 can call when data is updated.

The progress-note module 818 is configured and knows how to render different types of components of the electronic form. This rendering of different component of the progress note form allows the electronic form to be visually presented to a user, for example at the user device 16. Rendering performed by the progress-note module 818 may be entirely recursive. For example, the progress-note module 818 may recurse through blocks, panels, lists, etc. Rendering of the various components by the progress-note module 818 will now be described.

Using the received JSON, the progress-note module 818 generates rendered content blocks 820a, 820b, 820c. The rendered content blocks 820a to 820c are referred to collectively herein as content blocks 820 and generically as content block 820. Rendered content blocks 820 are merely provided as examples, additional rendered content blocks may be generated by the progress-note module 818 based on the JSON.

The progress-note module 818 can render out widget components 822. A widget component 822 represents a section of a progress note (or other electronic form, as the case may be). Widget components 822 may have different looks in JSON and work differently visually. Different widget components 822 may render out differently. Widgets 822 can have multiple columns.

Widget components 822 may include, for example, a rendered panel 824, a rendered list 826, a rendered CML 828, or other rendered widget component types.

The progress-note module 818 can render out columns. For example, the progress-note module 818 can generate rendered columns 830a and 830b and rendered column 832. A rendered column can render a content block (e.g. content blocks 834).

A list, such as rendered list 826, may also render with a single column (e.g. rendered column 830c). This may be done for consistency and for embodiments which include multi-column lists.

At 864, the list 826 may be configured to update redux 854 to tell them when new rows are added.

The progress-note module 818 can render out content blocks. For example, the progress-note module 818 can generate rendered content blocks 834a, 834b, and 834c.

At 866, a content block, such as rendered content block 834a, can also render one or more widget components 822.

The progress-note module 818 can render out form components. For example, the progress-note module 818 can generate rendered form components 836a and 836b.

In some cases, a form component can render one or more child form components. For example, rendered form component 836a may render form component 836b, which is a child form component of form component 836a. In such a case, the form component 836a may be considered a "parent form component".

The progress-note module 818 can render out row elements 838. Example row elements 838 include a text input 840, a checkbox 842, a radio button 844, a dropdown 846, a date 848, a text area 850, and a time 852.

At 868, row elements 838 may be constantly updating and controlled by redux 854 of progress-note module 818.

Rendered list 826 may be able to update redux 854 to tell them when new rows are added.

Dotted lines 864 and 868 illustrate that when workflow 800 is implemented by the frontend 412 and as users make changes to the progress note electronic form at the user device 16, the frontend 412 is recording the changes to send to the progress notes backend 410 to save and store. In this way, the system knows how to update itself when changes are made to the electronic form (via input data provided to the form).

An example of how the electronic progress note system, and in particular the workflow 800, can be implemented in a clinical context will now be described. A clinician, such as a physician, may want to track a condition of a patient using an electronic clinical note form. In particular, the clinician may want to track a certain measurement, such as blood pressure, over time. For example, the clinician may want to measure the patient's blood pressure at a current time and every hour thereafter and record such measurements in the electronic clinical note form. Each time the patient's blood pressure is taken, the system may add a new row to a list in the form representing the patient's blood pressure measurements over time. This may include recording a different JSON. The different JSON recorded based on the changes to the progress note form is not part of the JSON template for the progress note form. The list is configured to be modular, where rows can be added in modular fashion by the system and are defined by JSON.

The progress-note module 818 includes the redux component 854 and the callback 858.

At 860, the progress-note module 818 can call the callback 858.

At 862, the updated data is passed back through Progress notes UX 810 to the progress notes backend 410.

Figure 9:
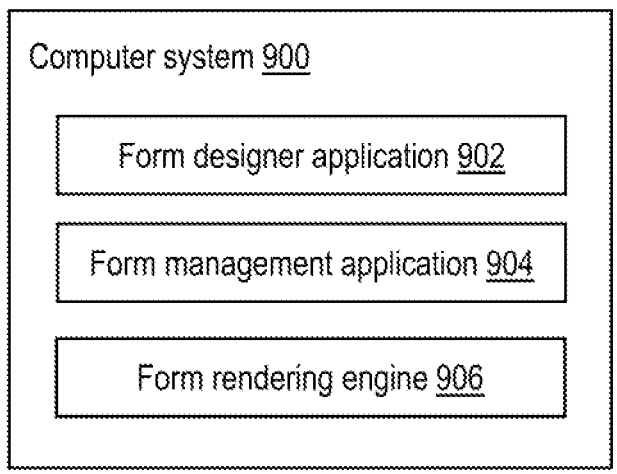
FIG. 9 is a block diagram of a computer system for creating, storing, updating, and visualizing a customizable structured dynamic electronic form, according to an embodiment.

Referring now to FIG. 9, shown therein is a computer system 900 for customizable structured dynamic electronic forms, according to an embodiment. The system 900 may be used to create, store, and update the electronic form. In an embodiment, the electronic form is a progress note. The computer system 900 may be implemented by components of system 10 of FIG. 1, such as the form management server 12, the form designer server 16, the end user device 14, and the client device 18. Features of system 900 may be included in other embodiments of the systems and methods described in the present disclosure.

The system 900 includes a form designer application 902. The form designer application 902 may include client side and server-side software components. The client-side software components may be implemented at the client device 18 and the server side software components may be implemented at the form designer server 16.

The form designer application 902 may include a form template preview function. The form template preview enables a user to see exactly how a progress note or other dynamic form will look, behave, and print without leaving the form designer application 902. The user may approve the form template based on the preview. For example, as the user is dragging and dropping form elements (modules, fields) to construct the form template, the user can see how the form behaves (i.e. test the dynamic components) before officially completing the template.

The system 900 also includes a form management application 904 and a form rendering engine 906. The form management application 904 and the form rendering engine 906 may include software components operating on the form management server 12, the end user device 14, or both. In an embodiment, the form management application 904 is a progress note management application such as PNapp (described herein) and the rendering engine 906 is a progress note rendering engine (such as FFE 718 or progress-note 818 described herein). The form rendering engine 906 may be a component of the form management application 904 or may be separate therefrom. The form management application 904 and form rendering engine 906 may be implemented as software components living inside another application or as a service. The service may be called through the use of API endpoints where specific API calls are made to provide certain functionalities of the components 904, 906, such as, for example, certain form modifications, form template modifications, or to return a specific form template, form data set, fully rendered form, or set of form rendering instructions.

Generally, the form designer application 902 generates a form template (e.g. progress note template). The form designer application 902 may then send the form template to the form management application 904 or the form rendering engine 906. The form management application 904 or form rendering engine 906 renders the form template. The form management application 904 may act as a middle man that sends the form template into the form rendering engine 906.

The rendering engine 906 renders and displays the form. Other applications can make use of the rendering engine, including applications other than the form management application 904.

The rendering engine 906 may include support for conditional logic. For example, the rendering engine 906 may include a conditional visibility function. In an example of the conditional visibility function, form designer application 902 may enable a user to drag in a dropdown list with different options (e.g. three choices). In other examples, techniques other than a dropdown list may be used to visually present options and enable their selection. Then, for any other panel or item the user drags into the form after the dropdown is added the user can add a "visible if" link. The visible if link allows the user to select options from the dropdown previously inserted into the form. This makes the panel only visible if parts of that dropdown are selected. In a progress note example, this feature may be used when a doctor is diagnosing a patient using a progress note form. Normally, the "panels" may be filled with clinical modules with checkboxes, text areas, and other input fields, of which there may be dozens. Not all clinical modules may need to be viewed (i.e. visible to the user) each time the form is used. This feature allows the form builder to link each module to an item in a dropdown list and then the user can review the dropdown list and check off the items that applicable to the patient. This way, the user does not have to scroll through unnecessary modules each time the user navigates the form.

In another example, the rendering engine 906 may include a conditional reordering function. The conditional reordering function controls in what order conditional modules are presented, matching the order with the order that the dropdown menu items are selected. So, in an example, if the dropdown lists "A, B, C" but the user selects "C" first, "B" second, and "A" third, the panels appear in order C, B, A.

The conditional logic functions of the form rendering engine 906 may be particularly advantageous as, in many instances of multi-use forms, the forms may look different or need access to different fields or sections of the form depending on how the form is filled out in that form instance, such as by hiding certain portions of the form until a certain value or field is entered. If data entered into a field is changed over time, it may be desirable to change how the form appears and/or the structure of the form itself as a consequence of how the user fills out the form (i.e. the form data entered into the form via user input), such as by showing or hiding certain other sections of the form, changing the order in which form elements are presented in the form, etc. Further, the conditional logic may enable a form to have one or more data fields control how another data field or fields may appear in the form (e.g. order relative to other fields, whether or not the field, element or component is rendered, font style or format).

The form rendering engine 906 may include added support for validation. This may include disallowing a user to save the form until any errors are fixed. Certain form fields, upon being added to the form by the user, may have validation restrictions placed on them (e.g. must fall within a certain range of values, must be a certain type of data, must be a certain date type or within a certain date ranges). Validation may include a concurrency feature. The form rendering engine 906 may be configured to implement a concurrency validation feature. The concurrency feature enables multiple users to work in the same form at once without undoing changes made by the other user(s). The concurrency feature may include one or more encoded rules about how a user is permitted to interact with the form instance when multiple users are working in the same form at the same time. The concurrency feature may include validation preventing a user from saving a value (or in some cases even entering a value) if another user is currently editing the same field in the same form instance already.

The form management application 904 may be configured to render the form. The form management application 904 may be further configured to save the feature and keep a history of changes to the form (i.e. changes to values input into the form). Users can submit the form, including the form data input by the user to the form, through the form management application 904. The form management application 904 uses the form rendering engine 906.

The form management application 904 may also include functionality enabling a user to select from among a plurality of available dynamic form templates (e.g. progress note form templates). For example, in a progress note context, different templates may be available to different users based on user site (e.g. a specific hospital may have a certain set of form templates available to its users).

The form management application 904 may further enable a user to view historical submitted forms (e.g. a history of completed and submitted notes). In the progress note context, this may include viewing a history of specific templates for specific patients.

The form management application 904 may include a submit form (e.g. progress note) feature. Once data has been entered into the dynamic form the user (e.g. clinician) can preview on the end user device what the dynamic form will look like (e.g. as a pdf). The user can submit the dynamic form using a secure PIN associated with the user. The form may then be watermarked and timestamped by the form management application 904. The form management application 904 may be configured to generate a plain text file version of the form. The plain text file can be viewed by the user and text contained therein can be copied and pasted into other software or systems.

The form management application 904 may be configured to generate a PDF of the form. The PDF may be saved to GCP and encrypted to prevent access to personal information (e.g. personal health information).

The form management application 904 may include an archive page function. The archive page function allows a user to view all submitted dynamic form PDFs (e.g. all submitted progress notes). As noted, submitted forms are stored by the system 900. A user, such as a clinician, can view any previously submitted forms (notes) that the user provided. The archive page function may include a search function for searching the archived forms whereby a user can search for a form template, then a specific note or all notes.

The form management application 904 may include a favourite template function. The favourite template function enables a user to set a favourite form template. The form management application 904 is configured to load the designated favourite template by default when the user opens the application 904.

The form management application 904 may include a site-specific template/notes function. Using this function, users may only have access to form templates and dynamic forms linked to their particular site (e.g. hospital or other clinical setting). For example, the user may belong to, and be identified in the system 900 as associated or linked with, one or more sites. The user may only be able to access form templates that are linked to the one or more sites with which the user is associated. The form management application 904 may retrieve and present a list of form templates available to the user, from which the user can provided user input data selecting the desired form template. In an example, a doctor may be provided with a list of available form templates for the hospital at which he or she works, and the doctor may then select the form template most relevant to the patient the doctor is assessing.

The form management application 904 may include an overwrite prevention function. Since the dynamic form is a "live document" in the sense that form data can be inputted to the form across multiple user sessions and the form is saved once a change is made to a field in the form, issues can arise when two users are in the form. For example, a first user may make a save to the form, preventing a second user also in the form from making a save to the form. In such a case, the second user is prompted with a warning and provided with the option of either abandoning their version of the form and loading the first user's version of the form, or the second user can download their changes to the form as a plain text file, open the first user's saved version of the form, and update the form using the second user's plain text changes to the form. This feature may advantageously avoid users working on and trying to save out-of-date versions of the form. The second user is thus prevented from overwriting the changes (or updates) to the form previously inputted and saved by the first user. This can be particularly critical in situations where multiple doctors are working on the same form template for the same patient.

While the above description provides examples of one or more apparatus, methods, or systems, it will be appreciated that other apparatus, methods, or systems may be within the scope of the claims as interpreted by one of skill in the art.

The invention claimed is:

1. A computer system for storing and visualizing structured dynamic electronic forms, the system comprising:
   a user device comprising a client form management application configured to:
      generate, in response to a user input, a first request for a dynamic electronic form, and send the first request to a computer server;

the computer server comprising a server form management application configured to:
   store the dynamic electronic form in memory, the dynamic electronic form comprising form template data and form data, the form data corresponding to input data inputted to the dynamic electronic form, wherein the form template data and the form data are stored separately, the form template data is stored in a first format, and the form data is stored in a second format;
   in response to the first request from the user device, merge
   the form template data and the form data and send the merged form template data and form data to the user device for rendering;
the client form management application further configured to:
   generate, based on form type data associated with the form template data and specifying a form type, a second request for a form filler package for the form type, the form filler package comprising rules for filling out and rendering the dynamic electronic form, the form filler package separate to the dynamic electronic form, and send the second request to the computer server;
the server form management application further configured to:
   in response to the second request, send the separate form filler package to the user device;
the client form management application further configured to:
   render, via a form rendering engine, the dynamic electronic form in a user interface using the merged form template data and form data and the separate form filler package, wherein the rendered dynamic electronic form includes a data entry field for receiving the form data.

2. The system of claim 1, wherein the first format is an unstructured format and the second format is a structured format.

3. The system of claim 1, wherein the form data stored at the computer server includes a history of values for the data entry field, the history of values comprising a plurality of values wherein each of the plurality of values correspond to input data entered into the data entry field during a different instance of use of the dynamic electronic form.

4. The system of claim 1, wherein the dynamic electronic form is configured to store a plurality of values for a given data entry field in the dynamic electronic form as a history of data values, each of the plurality of data values corresponding to input data received by the given data entry field during a different instance of use of the dynamic electronic form.

5. The system of claim 1, wherein the client form management application is further configured to send new form data inputted into the data entry field to the computer server for storage with the form data.

6. The system of claim 5, wherein the server form management application is further configured to store the new form data as a historical data value of the data entry field.

7. The system of claim 1, wherein the first request includes a first identifier linked to the form data and usable by the server form management application to retrieve the form data and a second identifier linked to the form template data and usable by the server form management application to retrieve the form template data.

8. The system of claim 7, wherein retrieving the form template data includes retrieving a latest template version of the form template data.

9. The system of claim 1, wherein the server form management application is further configured to convert the merged form template data and form data into a lightweight data exchange format prior to send to the user device.

10. The system of claim 7, wherein the server form management application uses the first identifier to determine whether the dynamic electronic form has existing form data and either retrieves the existing form data or creates a new dynamic electronic form based on the determination.

11. A computer device for structured dynamic electronic forms, the device comprising a processor and a memory in communication with the processor, the processor configured to execute a form management application to:
   store a dynamic electronic form including in memory, the dynamic electronic form comprising form template data and form data, the form data corresponding to input data inputted to the dynamic electronic form, wherein the form template data and the form data are stored separately, the form template data is stored in a first format, and the form data is stored in a second format;
   in response to a first request received from a user device, merge the form template data and the form data and send the merged form template data and form data to the user device for rendering; and
   in response to a second request from the user device requesting a form filler package corresponding to a form type of the dynamic electronic form, the form filler package separate to the dynamic electronic form, retrieve and send the separate form filler package to the user device, the separate form filler package comprising rules usable by a form rendering engine of the user device for filling out and rendering the dynamic electronic form, the dynamic electronic form including a data entry field for receiving the form data.

12. The device of claim 11, wherein the first format is an unstructured format and the second format is a structured format.

13. The device of claim 11, wherein the form data includes a history of values for the data entry field, the history of values comprising a plurality of values each of which correspond to input data entered into the data entry field during a different instance of use of the dynamic electronic form.

14. The device of claim 11, wherein the form management application is further configured to receive new form data from the user device and store the new form data as a historical data value of the data entry field.

15. The device of claim 11, wherein the first request includes a first identifier linked to the form data and usable by the form management application to retrieve the form data and a second identifier linked to the form template data and usable by the form management application to retrieve the form template data.

16. The device of claim 15, wherein the form management application uses the first identifier to determine whether the dynamic electronic form has existing form data and either retrieves the existing form data or creates a new dynamic electronic form based on the determination.

17. A computer-implemented method of storing and visualizing structured dynamic electronic forms, the method comprising:
   storing a dynamic electronic form at a computer server, the dynamic electronic form comprising form template data and form data, the form data corresponding to input data inputted to the dynamic electronic form, wherein the form template data and the form data are stored separately, the form template data is stored in a first format, and the form data is stored in a second format;

generating at a user device, in response to a user input, a first request requesting the dynamic electronic form, and sending the first request to the computer server;

in response to the first request from the user device, merging the form template data and the form data at the computer server and sending the merged form template data and form data from the computer server to the user device for rendering;

generating at the user device, based on form type data associated with the form template data and specifying a form type, a second request requesting a form filler package for the form type, the form filler package comprising rules on how to fill out and render the dynamic electronic form, the form filler package separate to the dynamic electronic form;

sending the second request from the user device to the computer server;

in response to the second request, sending the separate form filler package from the computer server to the user device; and rendering, at the user device, the dynamic electronic form in a user interface using the merged form template data and form data and the separate form filler package, the dynamic electronic form including a data entry field for receiving the form data.

18. The method of claim 17, wherein the first format is an unstructured format and the second format is a structured format.

19. The method of claim 17, wherein storing the form data at the computer server includes maintaining a history of values for the data entry field, the history of values comprising a plurality of values wherein each of the plurality of values correspond to input data entered into the data entry field during a different instance of use of the dynamic electronic form.

20. The method of claim 17, further comprising:

sending new form data inputted into the data entry field from the user device to the computer server for storage with the form data; and storing the new form data at the computer server as a historical data value of the data entry field.

* * * * *